(12) United States Patent
Skufca

(10) Patent No.: US 10,576,208 B2
(45) Date of Patent: Mar. 3, 2020

(54) DELIVERY SYSTEM FOR DELIVERING MEDICAL OR PHARMACEUTICAL COMPOUNDS

(71) Applicant: Peter Skufca, Tuebingen (DE)

(72) Inventor: Peter Skufca, Tuebingen (DE)

(*) Notice: Subject to any disclaimer, the term of this patent is extended or adjusted under 35 U.S.C. 154(b) by 514 days.

(21) Appl. No.: 15/240,858

(22) Filed: Aug. 18, 2016

(65) Prior Publication Data

US 2016/0354547 A1 Dec. 8, 2016

Related U.S. Application Data

(63) Continuation-in-part of application No. PCT/EP2014/053146, filed on Feb. 18, 2014.

(51) Int. Cl.
*A61M 5/28* (2006.01)
*B65B 3/04* (2006.01)
*A61M 5/31* (2006.01)

(52) U.S. Cl.
CPC ............ *A61M 5/288* (2013.01); *A61M 5/283* (2013.01); *A61M 2005/3139* (2013.01); *B65B 3/04* (2013.01)

(58) Field of Classification Search
CPC ........ A61J 1/201; A61J 1/2051; A61J 1/2065; A61J 1/2089; A61J 1/062; A61J 1/2013; A61M 5/288; A61M 5/283; A61M 5/008; B65B 3/04

See application file for complete search history.

(56) References Cited

U.S. PATENT DOCUMENTS

| | | |
|---|---|---|
| 3,413,975 A | 12/1968 Hein | 128/253 |
| 4,568,336 A | 2/1986 Cooper | 604/240 |

(Continued)

FOREIGN PATENT DOCUMENTS

| | | |
|---|---|---|
| DE | 1207043 B | 4/1962 |
| DE | 3924830 A1 | 7/1989 |

(Continued)

OTHER PUBLICATIONS

International Search Report of European Patent Office dated Nov. 5, 2014 in related International Application PCT/EP2014/053146 (9 pages).
International Organization for Standardization ISO 8362-1 standard for injection containers and accessories Part 1, third edition Dec. 15, 2009 [ISO 8362-1:2009(E)] (10 pages).

(Continued)

*Primary Examiner* — Ariana Zimbouski
(74) *Attorney, Agent, or Firm* — Imperium Patent Works; Darien K. Wallace

(57) ABSTRACT

A delivery system for delivering medical or pharmaceutical compounds includes a container, a closure element, an attachment element and a penetration element. The container contains the compounds and has a closed container bottom and an open second end. The closure element makes fluid-tight contact with the inner wall of the container. The penetration element has a hollow needle and moves along the longitudinal axis of the container. The penetration element includes a first link motion portion, and the attachment element includes a second link motion portion. One of the link motion portions is a projection, and the other is a guiding groove. As the projection moves in the guiding groove, the hollow needle of the penetration element moves towards the container bottom and penetrates the closure element. The penetration element moves inside the attachment element towards the container bottom based on how the projection travels in the guiding groove.

20 Claims, 18 Drawing Sheets

(56) References Cited

U.S. PATENT DOCUMENTS

| | | | | |
|---|---|---|---|---|
| 2008/0300536 A1* | 12/2008 | Wang | ............... | A61J 1/2089 604/89 |
| 2011/0319833 A1* | 12/2011 | Chun | ............... | A61M 5/326 604/198 |
| 2014/0102048 A1* | 4/2014 | Arnitz | ............... | A61M 5/008 53/467 |
| 2016/0051446 A1* | 2/2016 | Lev | ............... | A61J 1/2089 220/277 |

FOREIGN PATENT DOCUMENTS

| | | |
|---|---|---|
| DE | 19652708 A1 | 12/1996 |
| DE | 10121232 C2 | 4/2001 |
| DE | 10340613 A1 | 8/2003 |
| EP | 0298585 | 5/1988 |
| EP | 0312035 A2 | 10/1988 |
| EP | 0707859 A1 | 6/1995 |
| EP | 2535073 A1 | 6/2011 |

OTHER PUBLICATIONS

International Organization for Standardization ISO 8362-2 standard for injection containers and accessories Part 2, second edition Oct. 15, 2008 [ISO 8362-2:2008(E)] (10 pages).

International Organization for Standardization ISO 11040-4 standard for prefilled syringes Part 4, second edition Feb. 1, 2007 [ISO 11040-4:2007(E)] (14 pages).

International Organization for Standardization ISO 11040-5 standard for prefilled syringes Part 5, third edition Jan. 15, 2012 [ISO 11040-5:2012(E)] (10 pages).

* cited by examiner

DELIVERY SYSTEM FOR DELIVERING MEDICAL OR PHARMACEUTICAL COMPOUNDS

CROSS REFERENCE TO RELATED APPLICATION

This application is filed under 35 U.S.C. § 111(a) and is based on and hereby claims priority under 35 U.S.C. § 120 and § 365(c) from International Application No. PCT/EP2014/053146, filed on Feb. 18, 2014, and published as WO 2015/124173 A1 on Aug. 27, 2015. This application is a continuation-in-part of International Application No. PCT/EP2014/053146. International Application No. PCT/EP2014/053146 is pending as of the filing date of this application, and the United States is an elected state in International Application No. PCT/EP2014/053146, which is incorporated herein by reference.

TECHNICAL FIELD

The invention relates to a delivery system for delivering medical or pharmaceutical compounds.

BACKGROUND

A prior art delivery system for delivering medical or pharmaceutical compounds is described in EP2535073 A1 and includes a first container that stores the compounds, a closure element accommodated within the first container, and an extraction unit adapted to extract the compounds automatically once the closure element has been manually penetrated. In this known system, the first container is accommodated within a second container that serves, on the one hand, as a holding means for holding an energy unit used to carry out the above-mentioned automatic function and, on the other hand, as a support means to assist the first container in maintaining the extraction unit in a well-defined positional relationship with respect to the first container. That is, in order to put into effect the above-mentioned automatic delivery function, a container-container arrangement is provided that renders the overall structure complicated and accident-sensitive.

It is an object of the present invention to improve the reliability and easy applicability of the above known system by providing a delivery system for delivering medical and pharmaceutical compounds that dispenses with the above-mentioned automatic function.

SUMMARY

The present invention relates to a delivery system for delivering medical or pharmaceutical compounds that includes (a) a container unit with (a-a) a container for storing the compounds that has a circumferential wall, a first end closed by a container bottom and an open second end, wherein the container unit has a longitudinal axis, and (a-b) a closure element disposed within the container in a fluid-tight contact with the circumferential wall, and (b) an extraction unit that includes a penetration element having a hollow needle adapted to penetrate the closure element. The extraction unit is fitted to the container so as to be movable relative to the container along the longitudinal axis towards the container bottom. Furthermore, the extraction unit includes a first link motion portion, and the container includes a second link motion portion. One of the first or second link motion portions is provided with a projection, and the other one is provided with a guiding groove. The projection and the guiding groove are engageable with each other to form a link motion adapted to make the extraction unit move relative to the container in a predetermined way towards the container bottom, thereby making the hollow needle penetrate the closure element.

In another embodiment, a delivery system for delivering medical and pharmaceutical compounds includes a container unit and an extraction unit. The container unit includes a container and a closure element. The container is adapted to contain the compounds and has a cylindrical wall, a first end that is closed by a container bottom and a second end that is open. The closure element is disposed within the container and makes a fluid-tight contact with the cylindrical wall. The extraction unit includes a penetration element and a hollow needle adapted to penetrate the closure element. The extraction unit moves relative to the container along the longitudinal axis of the container unit towards the container bottom. The extraction unit includes a first link motion portion, and the container unit includes a second link motion portion. One of the first link motion portion or the second link motion portion is provided with a projection, and the other of the first link motion portion or the second link motion portion is provided with a guiding groove. The projection engages the guiding groove and guides the extraction unit to move relative to the container towards the container bottom so that the hollow needle penetrates the closure element at the longitudinal axis.

In one alternative arrangement, the container unit includes an attachment element attached to a rim portion of the container. The rim portion forms the second end of the container, and the second link motion portion is disposed on the attachment element. The penetration element extends through a through hole in the attachment element.

In yet another embodiment, a device includes a container, a closure element, an attachment element and a penetration element. The container is adapted to contain a liquid and has a cylindrical wall, a first end closed by a container bottom and a second end that is open. The closure element is disposed inside the container and makes fluid-tight contact with the cylindrical wall. The attachment element is attached to a rim portion of the container, and the rim portion forms the second end of the container. The attachment element has a guiding groove, and the penetration element has a projection. The penetration element also includes a grip portion and a hollow needle adapted to penetrate the closure element. The projection engages the guiding groove and guides the penetration element to move relative to the container towards the container bottom so that the hollow needle penetrates the closure element at the longitudinal axis. The guiding groove has a straight portion that runs parallel to the central longitudinal axis and a spiral portion. The closure element has a bottom surface with a first shape, and the container bottom has a second shape. The first shape and the second shape are complementary.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 7A is a schematic drawing showing a variation of the delivery system according to the present invention.

FIG. 7B is a schematic drawing showing another variation of the delivery system.

FIG. 7C is a schematic drawing showing yet another variation of the delivery system.

DETAILED DESCRIPTION

Reference will now be made in detail to some embodiments of the invention, examples of which are illustrated in the accompanying drawings. In the description and claims, terms such as "upper", "lower", "top", "bottom", "up", "down", "upwards" and "downwards" are used to describe relative directions and orientations between different parts of the system, and it is to be understood that the overall structure being described can actually be oriented in any way in three-dimensional space.

Figure 1A:
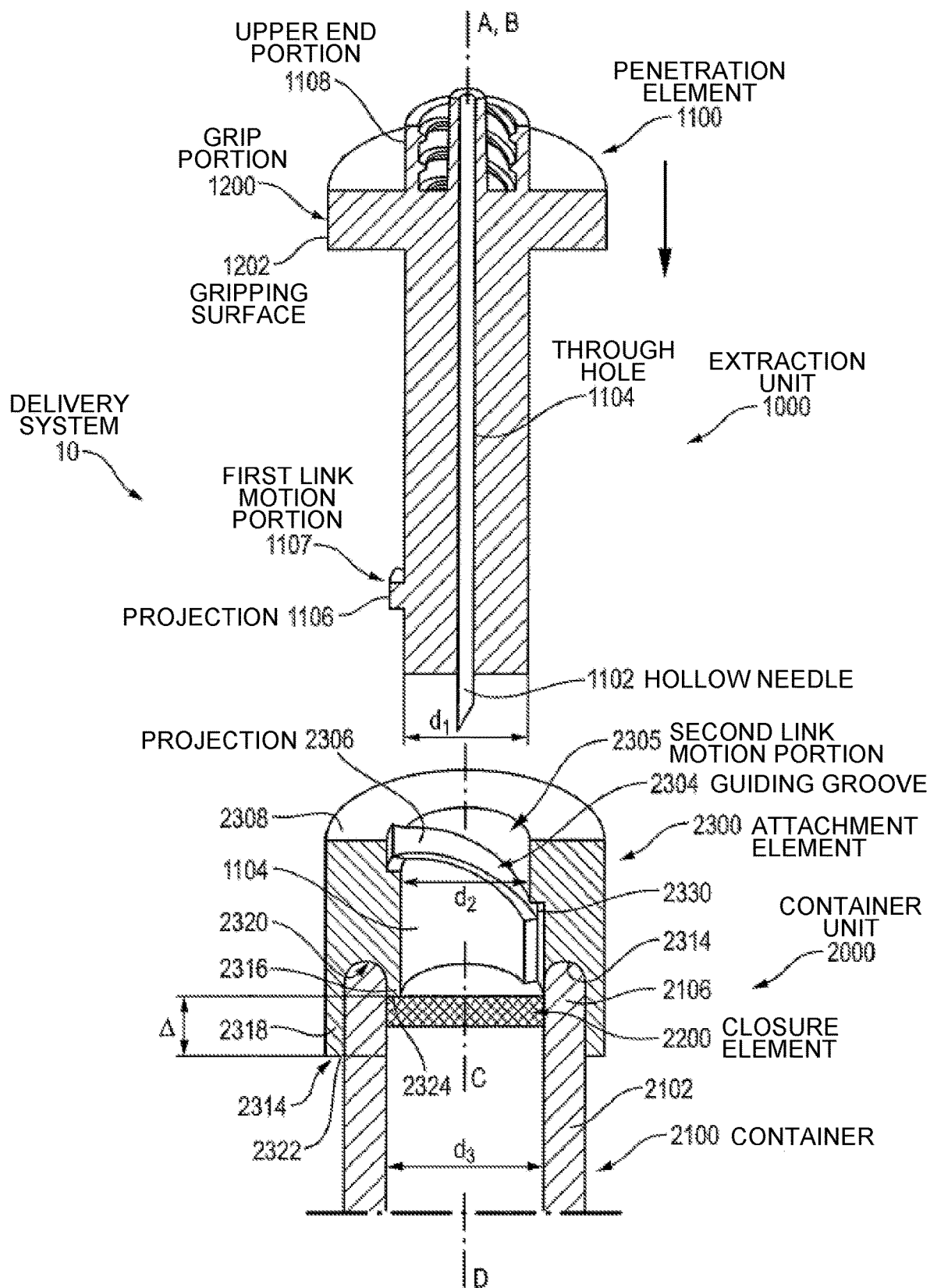
FIG. 1A is a schematic drawing of a delivery system in an initial position according to a first embodiment of the present invention.

FIG. 1A shows a delivery system 10 for delivering medical or pharmaceutical compounds. The delivery system includes a container unit 2000 and an extraction unit 1000. The container unit 2000 has a longitudinal axis A and includes a container 2100 and a closure element 2200. The container 2100 is used to store the compounds and has a circumferential side wall 2102, a first end closed by a container bottom 2104 and an open second end. The closure element 2200 is accommodated within the container 2100 and is in a fluid-tight contact with the circumferential wall 2102. The extraction unit 1000 includes a penetration element 1100 having a hollow needle 1102 adapted to penetrate the closure element 2200.

The extraction unit 1000 is fitted to the container 2100 so as to be movable relative to the container along the longitudinal axis A towards the container bottom 2104. The penetration element 1100 of the extraction unit 1000 includes a first link motion portion 1107, and the container 2100 includes a second link motion portion 2305. One of the first link motion portion 1107 or the second link motion portion 2305 is provided with a projection 1106, and the respective other one is provided with a guiding groove 2304. The projection 1106 and the guiding groove 2304 are engageable with each other and form a link motion adapted to make the extraction unit 1000 move relative to the container 2100 in a predetermined way towards the container bottom 2104, thereby making the hollow needle 1102 penetrate the closure element 2200. As the penetration element 1100 and its hollow needle 1102 are moved with the extraction unit 1000 relative to the container 2100, the motion link guides the hollow needle 1102 towards and into the closure element 2200, thereby making the hollow needle 1102 penetrate the closure element 2200.

The terms deliver, extract and discharge each emphasize a specific perspective. Deliver refers to the inventive system in its entirety in the general meaning of dispense or give off or the more specific meaning of administer in case of delivering compounds to an individual. Extract refers to the extraction unit 1000 in order to focus on the process or operation of removing or taking out the compounds without regard to the purpose of this process and irrespective of what is to be achieved with the compounds. Discharge refers to the transport of the compounds from the container 2100 through the hollow needle 1102 to the outside of the (entire) system, i.e., objectively to the penetration element 1100.

The medical and pharmaceutical compounds are liquid solutions that are in contact with the container 2100 and the closure element 2200. Therefore, the container 2100 together with the closure element 2200 forms a primary packaging for the compounds in conformity with the Guidelines on Packaging for Pharmaceutical Products, issued in the WHO Technical Report Series, No. 902, 2002, which provide that a primary packaging must protect the pharmaceutical or medical products against all adverse external influences that may affect their quality or potency such as, for example, light, moisture, oxygen, biological contamination or mechanical damage. In particular, such a primary packaging must not interact physically or chemically with the contained medical or pharmaceutical compounds in any way that would alter their quality. Specifically, a primary packaging must protect the contents from extraneous matter, from loss of the substance, and from efflorescence, deliquescence and evaporation under normal conditions of handling, shipping or storage.

The container 2100 and the closure element 2200 are parts of the container unit 2000. That is, the container unit 2000 includes at least these elements but may contain more than these elements. The container 2100 essentially has a right-cylindrical shape, i.e., the shape of a mathematical cylinder having its axis (the above-mentioned longitudinal axis A) perpendicular to its base. The container 2100 may be thought of as being made up of a tube or barrel (its circumferential or side wall 2102) of undefined cross-section, having its longitudinal axis perpendicular to each of the virtual planes closing its ends. Each virtual plane may be curved or bulged. One of the container ends is connected to or firmly closed by the container bottom 2104, such that the container bottom is not non-destructively removable. The container bottom 2104 may or may not completely lie within the virtual plane at the end of the container 2100. Preferably, the cross-section of the container 2100 is symmetric with respect to the longitudinal axis A so that the longitudinal axis is an axis of symmetry.

In order to enable handling and processing of the container 2100 in conventional filling facilities and with conventional technology used for filling and processing of standardized syringes, the container may meet, in terms of shape and dimensions, selected specifications of ISO 11040-4 standard of a prefilled syringe. All cross-sections perpendicular to the longitudinal axis A or axis of symmetry may be circles. Especially in this regard, the container 2100 may include or form a flange portion along its open second end.

The paragraphs below describe the preferred dimensions of the container according to various standards to which the container may comply. Following the terminology used in these standards, the container without the flange portion is called a barrel.

The cylindrical barrel complies, in terms of its inner diameter, outer diameter and wall thickness, with the relevant specifications of the above-mentioned ISO 11040-4 standard for a suitable specific standardized nominal volume. The specific standardized nominal volume may correspond to or may only slightly differ from, the predetermined filling volume of the container. Thus, the chosen volume of the container is a suitable one of the various nominal volumes provided by the ISO 11040-4 standard. In particular, the cylindrical barrel may be formed to meet the barrel diameters d1 and d2 and the barrel wall thickness s1 as indicated in FIG. 1 and Table 1 of the ISO 11040-4 standard for a specific standardized nominal volume of a standardized syringe. Depending on the predetermined filling volume, the length of the barrel may conform to the length 11 or total length l of a standardized syringe as indicated in FIG. 1 and Table B.1 of ISO 11040-4 standard, or may vary within a range defined by the length 11 and the total length l as aforementioned, or may even be different from the specifications of the ISO 11040-4 standard.

Generally, the length of the cylindrical barrel is defined and set so that the predetermined filling can be achieved with the inner diameter, outer diameter, and wall thickness adopted from the ISO 11040-4 standard for the specific nominal volume as above explained. If the predetermined filling volume matches a standardized nominal volume of a standardized syringe, the standardized nominal volume may be used as the specific nominal volume and the cylindrical barrel may be formed to meet the barrel diameters d1 and d2 and the barrel wall thickness s1 as indicated in FIG. 1 and Table 1 of the ISO 11040-4 standard for this standardized or specific nominal volume. In this case, the length of the barrel may meet the length 11 indicated in FIG. 1 and Table 1 of the ISO 11040-4 standard for the standardized nominal volume. If the predetermined filling volume differs from any of the nominal volumes set by the ISO 11040-4 standard, any suitable nominal volume close to the predetermined filling volume may be used as the specific nominal volume, and the cylindrical barrel may be formed to meet the barrel diameters d1 and d2 and the barrel wall thickness s1 as indicated in FIG. 1 and Table 1 of the ISO 11040-4 standard for this suitable or specific nominal volume.

Even if the predetermined filling volume matches a standardized nominal volume of a standardized syringe, however, any other suitable standardized nominal volume may be used as the specific nominal volume, and the cylindrical barrel may be formed to meet the barrel diameters d1 and d2 and the barrel wall thickness s1 as indicated in FIG. 1 and Table 1 of the ISO 11040-4 standard for this other standardized or specific nominal volume. For example, if the predetermined filling volume is 1 ml, the cylindrical barrel may meet the outer diameter d1, inner diameter d2, and wall thickness s1 of a 1 ml syringe in a long version, with d1 being 8.15 mm±0.1 mm, d2 being 6.35 mm±0.1 mm, and s1 being approximately 0.9 mm (cf. ISO 11040-4, Tables 1 and B.1 for a nominal volume of 1 ml). In this case, the barrel length may meet the length 11 of the 1 ml syringe in the long version, being 54 mm±0.5 mm, with the specific nominal volume being 1 ml. With the same predetermined filling volume of 1 ml, however, the cylindrical barrel may alternatively meet the outer diameter d1 (=10.85 mm±0.1 mm), inner diameter d2 (=8.65 mm±0.2 mm), and wall thickness s1 (•1.1 mm) of a 1 ml syringe in a short/standard version (cf. ISO 11040-4, Tables 1 and B.1 for a nominal volume of 1 ml) with the specific nominal volume being 1 ml, or may meet the outer diameter d1 (=6.85 mm±0.1 mm), inner diameter d2 (=4.65 mm±0.1 mm), and wall thickness s1 (•1.1 mm) of a 0.5 ml syringe (cf. ISO 11040-4, Tables 1 and B.1 for a nominal volume of 0.5 ml) with the specific nominal volume being 0.5 ml. In these alternative cases, the barrel length is appropriately adjusted so as to ensure that the container provides the predetermined filling volume.

Furthermore, the above-mentioned flange portion put on top of the cylindrical barrel may form, in a circumferential direction, a continuous circular flange, e.g., in line with the flange of a conventional vial according to the ISO 8362-1 standard. The flange portion may be in line with a form B of a finger flange of a standardized syringe (cf. ISO 11040-4, FIG. 1, Form B). Additionally, the flange portion may be formed to comply, in terms of its cross-sectional shape, with relevant specifications of the above mentioned ISO 8362-1 standard. The flange portion may meet, in terms of its axial length/height, in terms of its upper inner edge, and/or in terms of its upper end surface, the relevant specifications as indicated in FIG. 1, FIG. 2, FIG. 3 and Table 1 of the ISO 8362-1 standard. Specifically, the axial length/height of the flange may amount to 3.6 mm±0.2 mm, the bevel angle of the upper inner edge may be approximately 45°, and/or the taper angle of the upper end surface of the flange may be 3°±2° (cf. ISO 8362-1, FIGS. 1 to 3).

While the above-mentioned 3.6 mm±0.2 mm adopted from the ISO 8362-1 standard are preferable, the axial length/height of the flange portion may slightly differ from this standardized dimension as long as the flange portion still meets the following two functions: firstly, the flange portion shall enable handling and processing the container in conventional filling facilities and with conventional technology used for filling and processing of standardized syringes, i.e., the flange portion shall meet the function of a finger flange of a standardized syringe (cf. ISO 11040-4, FIG. 1); and secondly the design of the flange portion shall allow a precise fitting of the container to the extraction element. Further, the flange portion may differ, in terms of its inner diameter, outer diameter and its lower end surface, from the relevant specifications of the ISO 8362-1 standard (cf. ISO 8362-1, FIG. 1: diameter d4, diameter d2) in order to enable the flange portion to smoothly match the respective barrel dimensions. In particular, the flange portion may have a radially extending flat lower end surface unlike a standardized vial that has a tapered lower surface (cf. ISO 8362-1, FIGS. 1 to 3 showing a taper angle of 10°±5°). A flat lower end surface may facilitate the handling of the container in conventional filling facilities and with conventional technology used for filling and processing of standardized syringes. Generally, however, the lower end surface of the flange portion may be formed with a taper angle as it is known from ISO 8362-1 (cf. FIGS. 1 to 3 showing a taper angle of 10°±5°).

Accordingly, unlike a conventional vial, the container, in particular if used as a primary packaging may have at its outer surface no such neck constriction as specified in the ISO 8362-1 standard (cf. ISO 8362-1, FIGS. 1 to 3: diameter d3, height h3). On the other hand, the inner surface of the container may be finished at the upper end, i.e., the upper end section opposite the flange portion, in line with the finish of any appropriate one of vial models A, B, or C of the ISO 8362-1 standard (cf. ISO 8362-1, FIGS. 1 to 3). Specifically, the inventive flange may at least be as thick as that of a standard prefilled syringe.

The closure element 2200 is accommodated within the container 2100 in a fluid-tight contact with the circumferential wall 2102. In other words, the closure element 2200 is held by friction within the container 2100. To this end, the closure element 2200 may preferably be formed so as to be elastically deformable. The closure element 2200, prior to being penetrated by the hollow needle 1102 in the process of delivery of the compounds contained in the container 2100, seals the container 2100 in a fluid-tight, compound-tight and antiseptic manner by forming a leak-proof circumferential contact with its circumferential inner surface. In a preferred embodiment, once the closure element 2200 has been penetrated and the extraction unit 1000 is in abutting contact with the closure element 2200, the closure element 2200 can be pushed by the penetration element 1100 against the frictional force towards the container bottom 2104 to displace and discharge the medical or pharmaceutical compound from the container 2100 into the hollow needle 1102. Accordingly, in this preferred embodiment, the extraction unit 1000 and preferably the penetration element 1100 of the extraction unit 1000 may serve as a piston adapted to slide or move the closure element 2200 towards the container bottom 2104 to displace and discharge the medical or pharmaceutical compound from the container 2100 into the hollow needle 1102.

In an alternative preferred embodiment, once the closure element 2200 has been penetrated and the extraction unit 1000 is in abutting contact with the closure element, the closure element may remain with the extraction unit 1000 in an initial position. The closure element 2200 need not be pushed by the extraction unit 1000 against the frictional force towards the container bottom 2104, and the medical or pharmaceutical compounds can be drawn from the container 2100 into the hollow needle 1102 by applying a negative pressure to the container 2100 via the hollow needle 1102. Alternatively, the liquid solution of compounds may flow out of the container 2100 by gravitational force. In all of the above-mentioned embodiments, the closure element 2200 is penetrated. However, the fluid-tight contact between an outer circumference of the closure element 2200 and the inner surface of the container 2100 is such that a force greater than a penetration force for penetrating the closure element is needed to move the closure element towards the container bottom 2104. Therefore, the closure element 2200 and the container 2100 together form a sort of slide-press-fit.

The closure element 2200 may have a through hole 1104 aligned with the hollow needle 1102 and closed on either one side by means of a diaphragm. In such a case, as a matter of course, only the diaphragm has to be penetrated. The penetration element 1100 serves to penetrate the closure element 2200 and thereby to activate the delivery system 10 so as to enable the extraction and delivery of the compounds stored in the container 2100 and to extract the compounds. To this end, the extraction unit 1000 includes any kind of a penetration element that has, i.e., supports, holds and/or forms, a hollow needle. By penetrating the closure element 2200, the sterile storage of the compounds is undone at the point of penetration (and only there). In this regard, the hollow needle 1102 may at least partially extend through a through hole 1104 extending through the penetration element 1100 along the longitudinal axis. Furthermore, as mentioned above, the penetration element 1100 may serve to slide or move the closure element 2200 towards the container bottom 2104 in order to displace and discharge the medical or pharmaceutical compound from the container 2100 into the hollow needle 1102. The penetration element 1100 has an elongated structure with a cross-section smaller than a cross-section of the closure element 2200 and of the container 2100 in order to plunge or enter into the container.

Furthermore, the hollow needle 1102 may at least partially extend through a through-hole of the hollow needle 1102 supporting portion. The hollow needle 1102 preferably extends to only such an extent into the penetration element 1100 that a safe support is assured or may extend completely through the through hole 1104, projecting out of it or not at the other end of the hollow needle 1102 supporting portion. The through hole 1104 in the former case is formed as a stepped hole, having a first portion accommodating the hollow needle 1102, and a second portion having a diameter essentially equal to the inner diameter of the hollow needle 1102 in order for a fluid channel formed within the hollow needle 1102 supporting portion to have an essentially constant diameter.

The hollow needle 1102 serves to penetrate the closure element 2200 and, to this end, protrudes, projects or juts out from an end face of the penetration element 1100 opposite or facing the container bottom 2104 parallel to and preferably aligned with the longitudinal axis A. The hollow needle 1102 is firmly held by the penetration element 1100, preferably extending into it by a predetermined amount assuring its firm position specifically in the process of penetration. The term hollow needle refers to the hollow needle 1102 used to penetrate the closure element 2200, whereas the term cannula used later refers to a hollow needle for application or administration of the compounds, which is arranged on the patient side, for example.

The link motion is defined between the first and second link motion portions of the extraction unit 1000, which is preferably between the penetration element 1100 and the container 2100. The first link motion portion 1107 is provided at the penetration element 1100, while the second link motion portion 2305 is provided at the container 2100. One of the link motion portions may be provided with one of the projection 1106 and the guiding groove 2304, while the other of the link motion portions may be provided with the other of the projection 1106 and the guiding groove 2304. Thus, the extraction unit 1000 is coupled to the container 2100 by means of the link motion, i.e., by the first link motion portion 1107 and the second link motion portion 2305. In other words, the link motion is a form-locking connection that the extraction unit 1000 forms with the container 2100. The form-locking connection realized by the link motion between the first link motion portion 1107 and the second link motion portion 2305 prevents any unintended or accidental separation of the extraction unit 1000, more specifically any separation of the penetration element 1100 with the hollow needle 1102 and the container 2100.

The link motion is a detachable, unlockable or removable link or connection between the penetration element 1100 and the closure element 2200. Either of the penetration element 1100 or the supporting element can be provided with a slide block, i.e., a pin or peg, which is a projection that is moved along a predetermined trajectory by the guiding groove 2304 arranged in either the penetration element 1100 or the supporting element. Thus, the inventive motion is not a screw joint. The term link motion is sometimes and synonymously called motion link. Both terms refer to a structure and not to a type of motion, as the first term might suggest. Specifically, the motion of one of the first and second link motion portions as a whole with respect to the other one of the first and second link motion portions follows the guiding groove 2304. This may be achieved if the projection 1106 as part of the one link motion portion is an element that is inflexible and steadfastly connected, preferably integrally connected, to a main body of the one link motion portion. Alternatively, the projection 1106 may in principle be flexibly connected to the main body of the one link motion portion in the way of any conventional ballpoint mechanism where a ballpoint refill is linearly movable while a projection of a compression piece thereof, usually activated by a thumb of a user to move the refill in and out, is flexible. Usually, in such a ballpoint mechanism, the compression piece is pressed once to move out the refill, and is removed in by pressing the compression piece a second time. Therefore, according to a preferred aspect of the present invention, the link motion may be designed in line with such a ballpoint mechanism.

In the latter case, the extraction unit 1000 may preferably be elastically biased relative to the container 2100 in a direction opposite to the needle penetration direction. The needle penetration direction is the moving direction of the first link motion portion 1107, i.e., of the penetration element 1100 and of the hollow needle 1102, with respect to the second link motion portion 2305, i.e., the container 2100, and the closure element 2200. An elastic force biasing the extraction unit 1000 in a direction opposite to the penetration direction may be achieved by an elastic restoring force of the closure while penetrating the closure element 2200. Alternatively, the elastic force may be achieved by providing an elastic element, such as a compression spring, between the extraction unit 1000 and the container 2100, or in functional terms between the first link motion portion 1107 and second link motion portion 2305.

The shape of the guiding groove 2304 and, therefore, the trajectory of the projection 1106 is not limited in any way. The guiding groove 2304 may generally have the shape of a regular spiral, i.e., a helical curve, or may be curved in any other way, or may be just straight, or may form spiral, curved and/or straight guiding groove sections. In other words, the guiding groove may extend linearly along and/or rotationally around the longitudinal axis A so as to define a predetermined way of movement of the projection 1106, which extends linearly along and/or rotationally around the longitudinal axis A. A straight guiding groove is the simplest form of a guiding groove and nevertheless has the advantage that the penetration element 1100 cannot be retracted once the closure element 2200 has been penetrated. Therefore, the delivery system 10 can be depolluted as a whole, without the danger of contaminating something with its former compounds.

The first link motion portion 1107 is located at the penetration element 1100. The first link motion portion 1107 may be inserted into the second link motion portion 2305. The second link motion portion 2305 is formed as a corresponding recess or blind hole provided in the container 2100 so as to receive the first link motion portion 1107 projecting from the penetration element 1100. In the broadest sense, the delivery system 10 merely requires the link motion to be formed between the first and second link motion portions. Because any link motion composed of two components implies that one of these is inserted into the respective other one, this aspect defines a specific spatial relationship as shown in FIG. 1A. Alternatively, the closure element 2200 can be formed such that the second link motion portion 2305 extends into the penetration element 1100, and the first link motion portion 1107 is formed as a hole. In both cases, the projection 1106 can be in either in the penetration element 1100 or in the attachment element 2300.

The second link motion portion 2305 is arranged in an attachment element 2300 attached to a rim portion of the container 2100 that forms the open second end. The attachment element 2300 serves to connect, mount or fit the extraction unit 1000 to the container 2100 and may, therefore, be regarded as an adapter that is part of the container unit 2000. The attachment element 2300 also performs the function of dimensional adaptation allowing the design to be individually optimized to some extend. The attachment element 2300 aligns the extraction unit 1000 with respect to the container 2100 and guides the extraction unit 1000, using the link motion portion, in the process of attaching the extraction unit 1000 and penetrating the closure element 2200 with the hollow needle 1102. The penetration element 1100 extends through a through hole 2302 of the attachment element 2300. The penetration element 1100 and the through hole 2302 are radially dimensioned to form a loose fit. The attachment element 2300 may be formed as a ring-shaped cap surrounding the penetration element 1100.

Alternatively, when diameters are used to define the dimensions, the diameter of the penetration element 1100 is smaller but essentially equal to the diameter of the through hole 2302. The diameter is defined in a plane perpendicular to the longitudinal axis, and the guiding groove 2304 and the projection 1106 are disregarded. Thus, the through hole 2302 of the attachment portion ensures that the link portion is stably positioned and guided.

The attachment element 2300 has a first overlapping portion outwardly overlapping the container 2100. The attachment element 2300 has a second overlapping portion inwardly overlapping the container 2100. In a longitudinal section including the longitudinal axis A of the container 2100, the attachment element 2300 overlaps the container 2100 in a U-shape in case of inwardly and outwardly overlapping the container, where the legs of the U (the l-portions thereof) may be of equal or different length. At least the first overlapping portion may be of an elastic material.

Due to its elasticity, the first overlapping portion can be placed on or pulled over the open second end of the container 2100 in a taut or stretched state to establish a tight but detachable press-fit. Preferably, the first overlapping portion is made of rubber or elastic plastic. A portion of the attachment element 2300 that forms part of the second link motion portion 2305 is made of a non-elastic material. The non-elastic material of that portion provides a stable form and enables the smooth rotational-translational movement of the penetration element 1100 (specifically the hollow needle supporting portion) with respect to and within the attachment element 2300. The contact surfaces of the penetration element 1100 and the attachment element 2300 are smooth, and their respective materials are selected so that the friction between them is minimized. The attachment element 2300 may include an inset that is glued into the main body of the attachment element and is made of the non-elastic material to provide a stable form.

The extraction unit 1000 includes a grip portion 1200 connected to the penetration element 1100. The penetration element 1100 and the grip portion 1200 are integrally formed or formed in a one-piece fashion. The grip portion 1200 is provided with a knurled surface that has indentations and/or projections that allow the penetration element 1100 to be held firmly in the process of penetrating the closure element 2200 with the hollow needle 1102. The outer circumference of the grip portion 1200 has the shape of a circular cylinder. Alternatively, the shape of the grip portion 1200 is polygonal in cross-section. The hollow needle supporting portion firmly holds the hollow needle 1102 in a well-defined position. The firm attachment is achieved by press-fitting or gluing the hollow needle 1102 into a through hole 1104 that extends through the penetration element 1100.

The extraction unit 1000 has a delivery end formed as a part of a Luer lock connector. The Luer lock connector is a preferred design because of its standardization. The Luer lock connector connects the delivery system 10 to another device or to a human body or the body of an animal. The part of a Luer lock connector that is part of the delivery system 10 may be formed as either the female or the male part thereof.

The extraction unit 1000 has a delivery end formed as a spray valve 1114 in which the unit has no cannula. Instead, the blunt end portion of the hollow needle 1102 (the end portion opposite to the lower sharp end portion) transitions or blends into the spray valve 1114. The blunt end portion of the hollow needle 1102 is formed as the spray valve 1114. Alternatively, the spray valve 1114 is a separate component attached to or inserted into the channel extending through the penetration element 1100. The spray valve 1114 is recessed or set back into an upper or outer surface of the penetration element 1100 in order not to protrude therefrom.

In another embodiment, the extraction unit 1000 has a delivery end formed as a cannula. A cannula is a hollow needle adapted to be plugged on a syringe to put a medical fluid into a human being or an animal, mostly intravenously. Preferably, the cannula is of a type that allows the use of the delivery system 10 as an infusion system. For example, the cannula allows a flow of air into the container 2100 and, thereby, a flow of the compounds out of the container solely by gravitation. The term "to extract" used above may in this case be replaced by "to empty" in view of the passive draining of the compounds, i.e., the draining without the help of some kind of actuator.

The container 2100 has a flange extending along the open second end, and the first overlapping portion of the attachment element 2300 has a circular groove 2320 adapted to accommodate the flange. The ring-shaped flange extends outwardly into the groove, which is complementarily shaped to the extent required to establish a reliable fit. If the first overlapping portion is rubber-like, it can be placed over the flange while the flange snaps into the groove. The attachment improves the fit of the cap on the container 2100, i.e., the connection between both.

The contact surfaces of the container bottom 2104 and the closure element 2200 are complementarily shaped to account for the condition in which the closure element 2200 is pushed by the penetration element 1100 to the container bottom 2104. At least one of these contact surfaces includes a blind hole 2108, 2202 that accommodates the tip of the hollow needle 1102.

The tip of the hollow needle 1102 fits in the blind hole 2202 while a force along the longitudinal axis A is transmitted from the penetration element 1100 to the closure element 2200 and moves the closure element towards the container bottom 2104. The term complementarily shaped means that opposing surfaces of the closure element 2200 and the container bottom 2104 are configured such that they are essentially in surface contact with each other when the piston portion (penetration element 1100) is located at its most downward position (i.e., when the compounds initially contained in the container 2100 have been extracted as much as possible with the hollow needle 1102 in a complete extraction allowing position). As used above, "essentially" means except for a depression or recession (blind hold) that is formed in one or both of them. Thus, the contact surfaces are essentially parallel to each other (except for the depression). Any convexity of one of the contact surfaces corresponds to the concave mirror image of the other one of the contact surfaces.

The contact surfaces are generally flat-shaped or ellipsoidically or spherically shaped. The shapes of the contact surfaces are variations in terms of their respective manufacturing process as well as for the extraction efficiency they allow. Nevertheless, the contact surfaces may be shaped arbitrarily. Preferably, the ellipsoidically or spherically shaped contract surfaces are disposed such that their respective axis of symmetry is aligned with the longitudinal axis A.

The guiding groove 2304 extends linearly along and/or around (i.e., rotationally around) the longitudinal axis A. The guiding groove 2304 may be formed such that a relative movement of the penetration element 1100 with respect to the mounting element is carried out by (i) rotating and/or linearly advancing the extraction unit 1000 along the longitudinal axis A to longitudinally move the hollow needle 1102 by a first distance (h2) to make the hollow needle 1102 penetrate the closure element 2200, and (ii) further rotating the extraction unit 1000 to longitudinally move the hollow needle 1102 by a second distance (h2−h1) to retract the hollow needle 1102 to a complete extraction allowing position.

The complete extraction allowing position is a position that allows the extraction of essentially all of the compounds stored in the container 2100 to be extracted. First of all, this position is determined in that, in the penetration process, the hollow needle 1102 has to completely penetrate the closure element 2200. Depending on the structure of the closure element 2200, the closure element has to be over-penetrated to some extent. In the case of a diaphragm, the diaphragm may be stretched and spring back. This over-penetration position is the position achieved by the first distance (h2). In this embodiment, the hollow needle 1102 is then retracted to the complete extraction allowing position (as for terminology, the over-penetration position may be called a complete penetration position). This position is achieved by the second distance (h2−h1, with h1<h2).

The small retraction of the hollow needle 1102 may serve to achieve a more or less complete extraction of the medical or pharmaceutical compound from the container 2100. Where the closure element 2200 is not moved towards the container bottom 2104, e.g., in the case of the above-mentioned alternative preferred embodiment shown in FIG. 4D), a retraction of the hollow needle 1102 prevents the hollow needle 1102 from extending beyond the closure element 2200 towards the container bottom 2104. Preventing such extension of the hollow needle 1102 beyond the closure element 2200 facilitates a more or less complete extraction of the medical or pharmaceutical compound from the container 2100.

The guiding groove 2304 may further be formed such that the relative movement of the extraction unit 1000 with respect to the container unit 2000 is further carried out by (iii) rotating the extraction unit 1000 to a locking position, preferably without any further longitudinal movement of the hollow needle 1102. The longitudinal locking position is a position in which the extraction system is longitudinally fixed. In the embodiment in which the closure element 2200 is to be moved, this position may also be called a longitudinal force transmittable position that allows a longitudinal force to be applied, i.e., a force along the longitudinal axis sufficient to move the closure element 2200. Thus, in a longitudinally locked state, the penetration element 1100 and the extraction unit 1000 are secured to the container unit 2000.

The delivery system 10 is a modular system that includes the extraction unit 1000 as a first module and the container unit 2000 as a second module. The first and second modules can be exchanged in case one of them is damaged or in case differently shaped containers and/or containers storing different compounds and/or differently shaped extraction units are to be used or in case one of them is to be cleaned in the sense of sterilized, as long as they are correspondingly shaped to be connectable, which is assured by the attachment unit. A user may order only a single first module used for a plurality of different compounds. The second module may include the container 2100, the attachment element 2300, and the closure element 2200 as a first, a second, and a third sub-module, respectively.

At least one of the modules may be sterilizable. The extraction unit 1000 is elastically biased in a direction away from the container unit 2000. The delivery system includes an elastic element arranged between the extraction unit 1000 and the container unit 2000.

FIG. 1A is a schematic drawing showing a first embodiment of a novel delivery system 10. The delivery system 10 includes an extraction unit 1000 and a container unit 2000. The extraction unit 1000 includes a penetration element 1100 and a grip portion 1200. The container unit 2000 includes a container 2100, a closure element 2200 and an attachment element 2300.

The penetration element 1100 serves as a hollow needle supporting portion and includes a hollow needle 1102. The hollow needle 1102 is mounted in a through channel or through hole 1104 of the penetration element 1100 in such a way that a longitudinal axis A of the penetration element 1100 and a longitudinal axis B of the hollow needle 1102 coincide. The hollow needle 1102 has a lower, chamfered end portion and an upper end on a level with an upper end face of the penetration element 1100. The penetration element 1100 also has a projection 1106 that is part of a first link motion portion 1107. An upper end portion 1108 of the penetration element 1100 is formed as a male part 1110 of a Luer lock connection. The upper end portion 1108 has a central, arbor-like projection that houses an upper portion of the channel 1104, which accommodates the hollow needle 1102.

FIG. 1A shows that the grip portion 1200 is integrally formed as one piece with the penetration element 1100. The grip portion 1200 is a ring surrounding the penetration element 1100 and extends laterally (i.e., perpendicular to the longitudinal axis A) outwardly from the penetration element 1100. The grip portion 1200 has a gripping surface 1202, which is a circular, band-shaped outer lateral surface. The gripping surface 1202 is textured to improve the grip or hold by the user's hand when the extraction unit 1000 is screwed into the attachment element 2300. Circular objects such as the grip portion 1200 appear elliptical in the drawings to represent a slight tilt of their upper surfaces. The actual shapes of the objects is not affected by the elliptical drawings.

The container 2100 has a hollow right-cylindrical shape and includes a tube-shaped side wall 2102 and a container bottom 2104 that closes the side wall 2102 at a lower end of the container, which is outside the view of FIG. 1. The side wall 2102 has a ring-shaped upper end portion 2106 that forms an open second end of the container 2100. The attachment element 2300 is part of the container unit 2000 and functions as a ring-shaped, cap-like adapter between the extraction unit 1000 and the container 2100. The attachment element 2300 has a through hole 2302 and a guiding groove 2304, which function as a second link motion portion 2305. The guiding groove 2304 extends in the through hole 2302 along the inner surface of the attachment element 2300. A projecting spiral groove portion 2306 is adapted engage and glide within the guiding groove 2304 so as to form a link motion that results in the rotational-translational movement of the penetration element 1100 and the extraction unit 1000 as a whole. The rotational-translational movement of the penetration element 1100 is with respect to the attachment element 2300 and container 2100 in a predetermined way towards the container bottom 2104. The guiding groove 2304 includes the spiral groove portion 2306 and a straight groove portion 2312. The spiral groove portion 2306 extends from a circular, ring-shaped upper surface 2308 of the attachment element 2300 and spirally winds around the longitudinal axis A to an inner point 2310. The straight groove portion 2312 connects to the spiral groove portion 2306 at the inner point 2310 and extends parallel to the longitudinal axis C of the attachment element 2300 to a lower surface 2314 thereof. The longitudinal axis C coincides with the axes A and B in a connected state of the penetration element 1100 to the attachment element 2300, as shown in FIGS. 1B and 1C.

FIG. 1A shows that the lower end portion of the attachment element 2300 is shaped such that it straddles the upper end portion 2106 of the container 2100. A ring-shaped inner portion 2316 of the attachment element 2300 extends less along an inner surface of the container 2100 towards the container bottom 2104 than an ring-shaped outer portion 2318 extends along an outer surface of the container 2100. Therefore, there is a longitudinal difference Δ between a circular lower edge of the inner portion 2316 and a circular lower edge of the outer portion 2318. As shown in FIG. 1A, the inner portion 2316 and the outer portion 2318 form a circular groove 2320 with a half-pipe-like roof. From an upside-down perspective, the circular groove 2320 forms a circular trough with walls of different wall heights. The lower surface 2314 of the attachment element 2300 is a sum of a ring-shaped outer end face 2322, a ring-shaped inner end face 2324 and the surface 2328 of the roof 2320. The circular groove 2320 serves to accommodate the end portion 2106 of the container 2100.

The closure element 2200 is formed from an elastic material and forms a fluid-tight contact with the inside of the container 2100, which seals the container 2100 until delivery of the compounds stored therein. In the initial position depicted in FIG. 1A, the closure element 2200 is not yet pressed down into the container 2100. In this embodiment, the closure element 2200 is formed as a circular, slightly elastic disc that is in contact with the end face 2324 of the attachment element 2300. The closure element 2200 fluid-tightly abuts or rests against the inner surface of the container 2100 due to the element's elasticity. In FIG. 1A, the penetration element 1100 is not yet coupled to or connected with the attachment element 2300, and the closure element 2200 has not yet been penetrated or pierced by the hollow needle 1102. The seal between the closure element 2200 and the container 2100 sterilely holds medical or pharmaceutical compounds stored therein. In this condition, the container 2100 together with the closure element 2200 forms a primary packaging as defined above.

FIG. 1A shows that the outer diameter d1 of the penetration element 1100, and an inner diameter d2 of the attachment element 2300 are essentially equal allowing the penetration element 1100 to fit snugly into the through hole 2302 of the attachment element 2300. In contrast, due to the inner portion 2316, the inner diameter d3 of the container 2100 is larger than each of the outer diameter d1 of the penetration element 1100 and the inner diameter of the attachment element 2300.

Figure 1B:
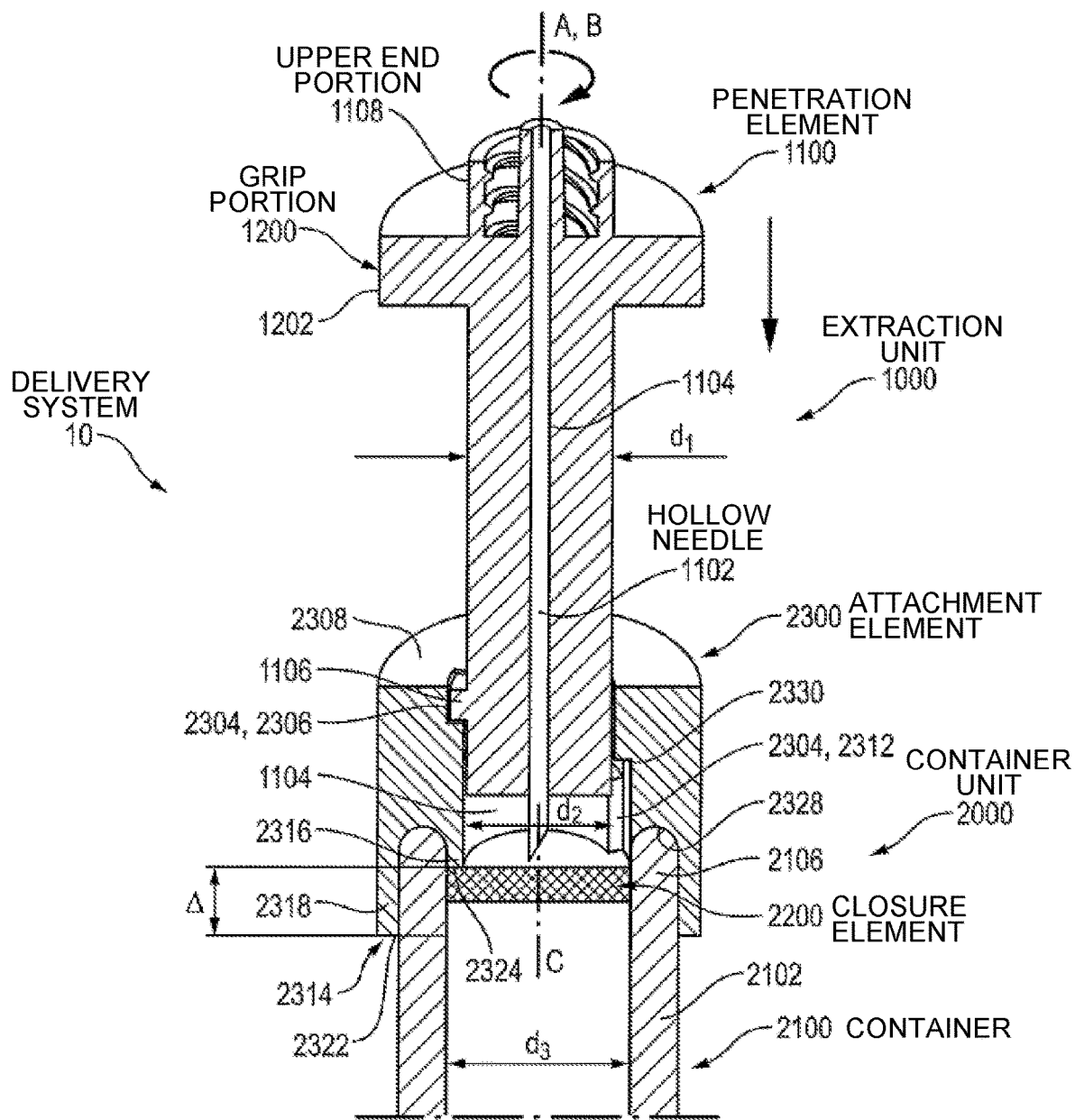
FIG. 1B is a schematic drawing of the delivery system of FIG. 1A in an intermediate state.
Figure 1C:
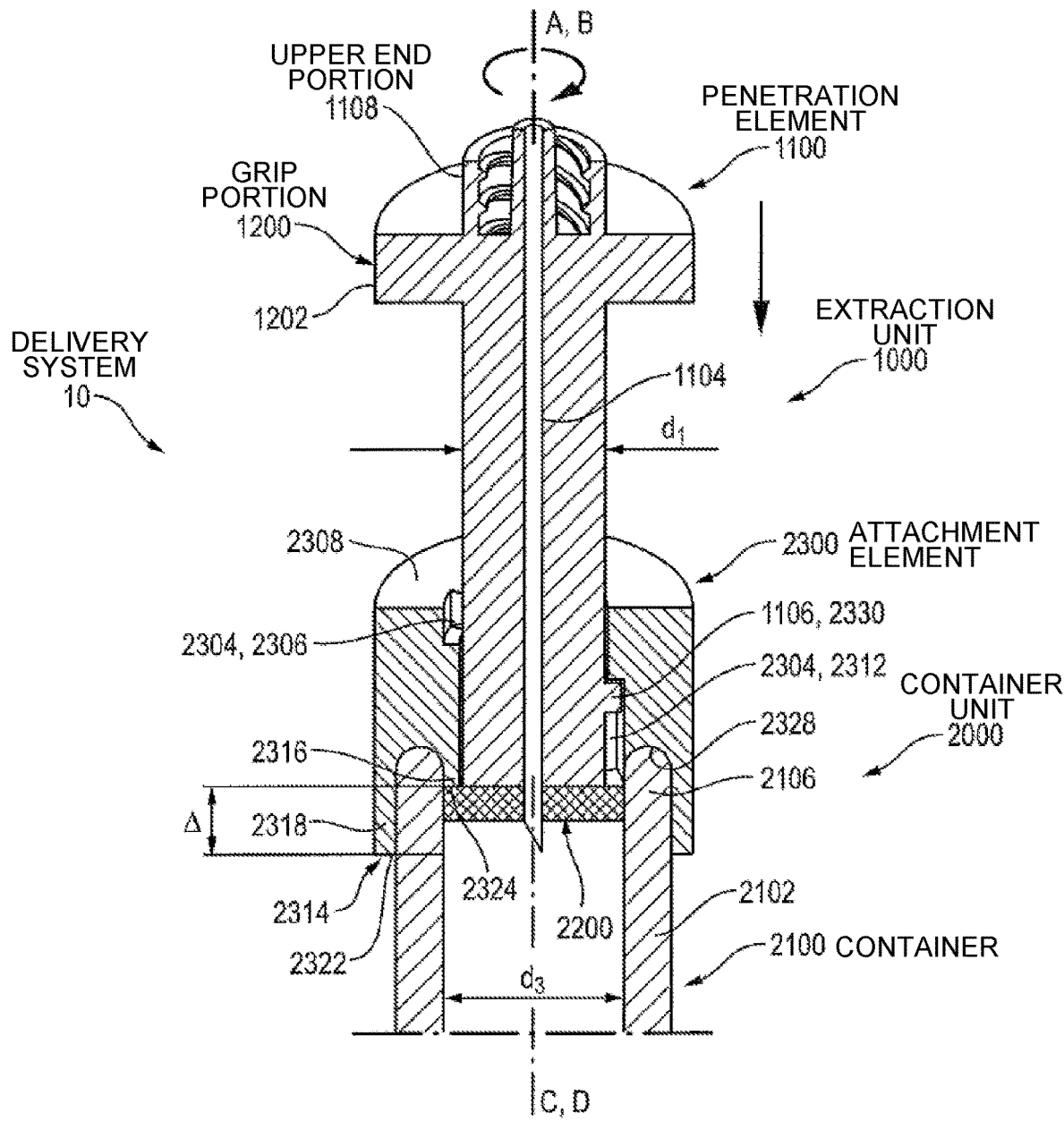
FIG. 1C is a schematic drawing of the delivery system of FIG. 1A in a completely penetrated state.
Figure 1D:
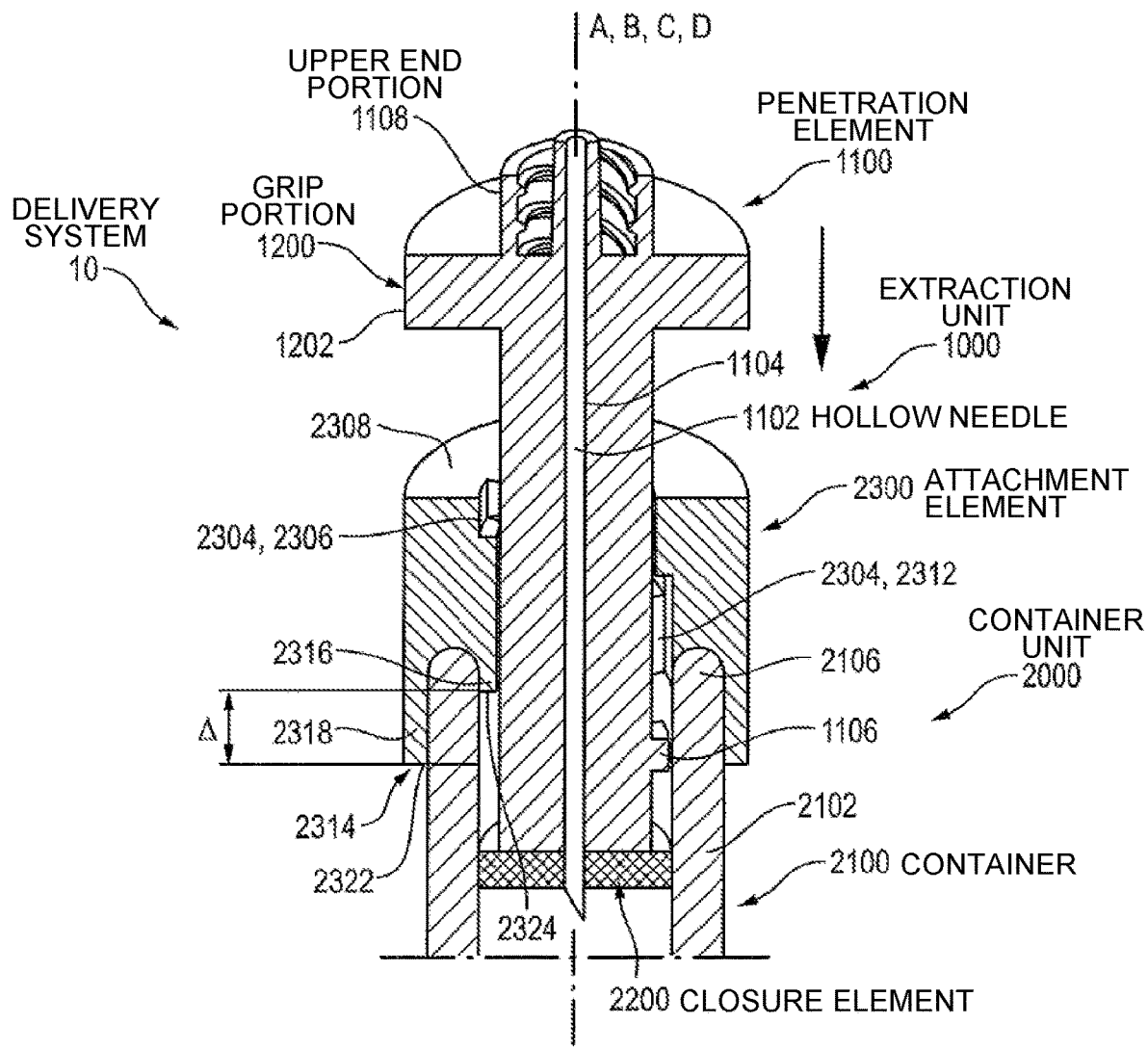
FIG. 1D is a schematic drawing of the delivery system of FIG. 1A with the closure element pushed towards the container bottom.
Figure 2A:
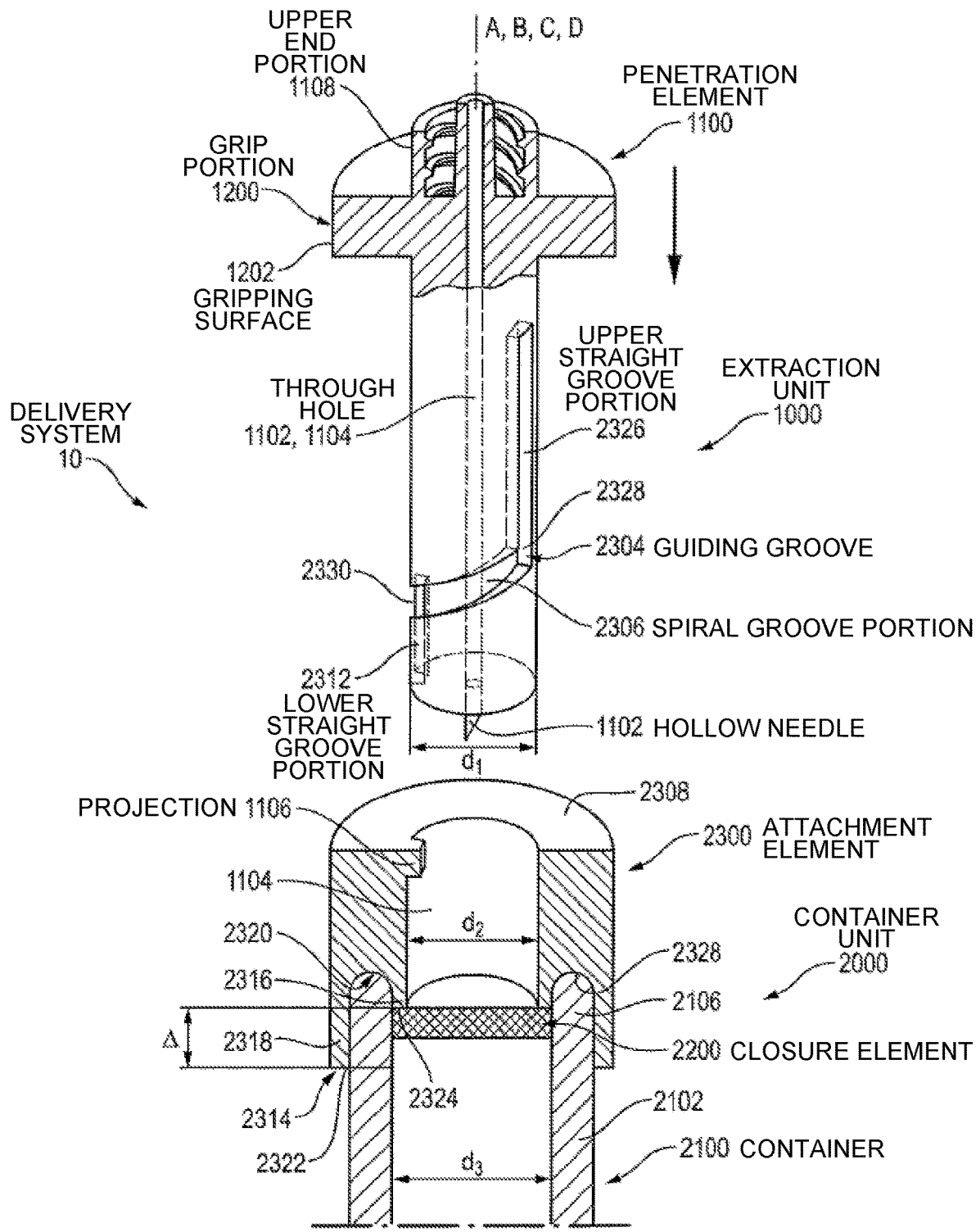
FIG. 2A is a schematic drawing of a delivery system in an initial position according to a second embodiment.
Figure 2B:
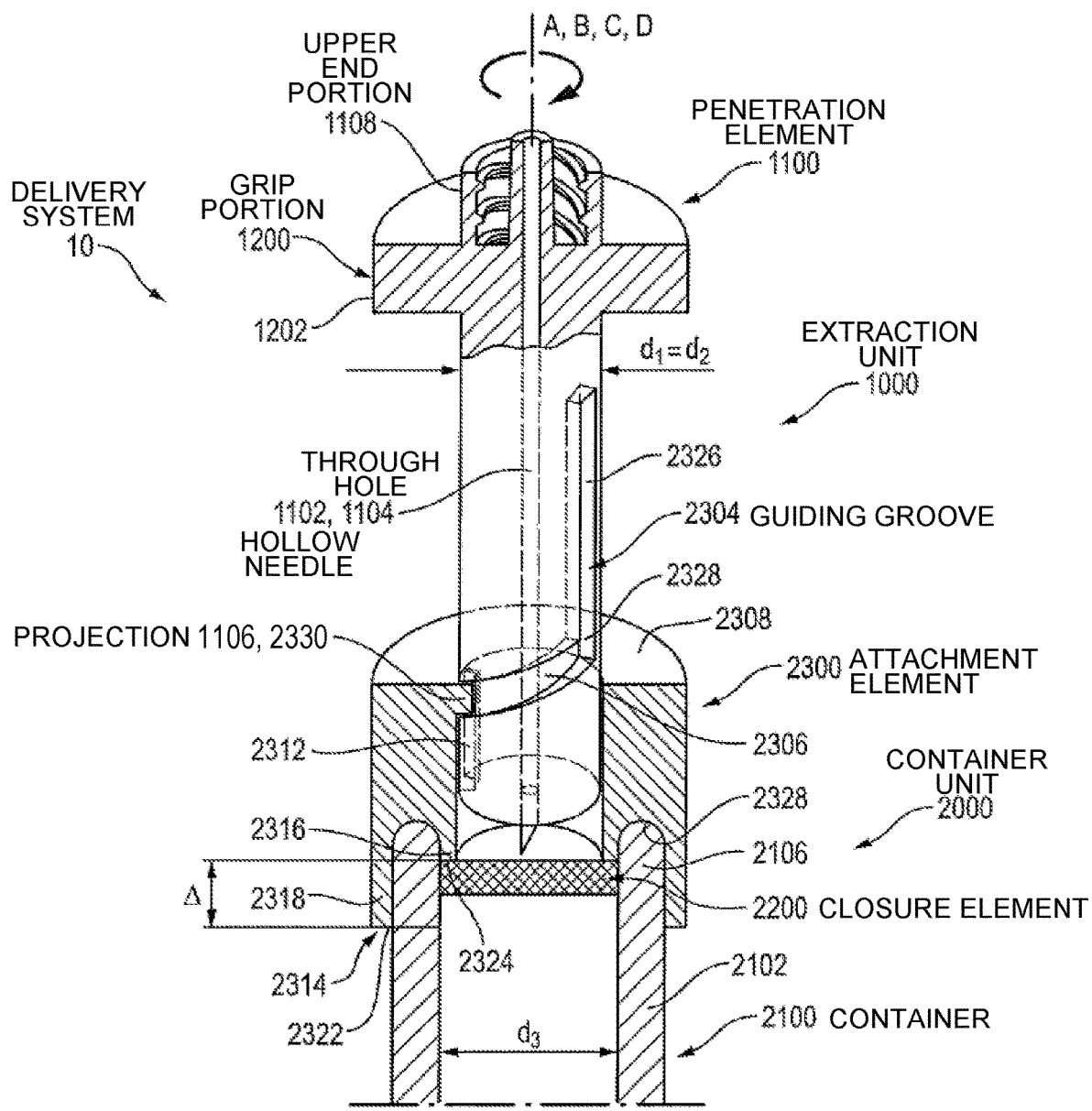
FIG. 2B is a schematic drawing of the delivery system of FIG. 2A in an intermediate state.
Figure 2C:
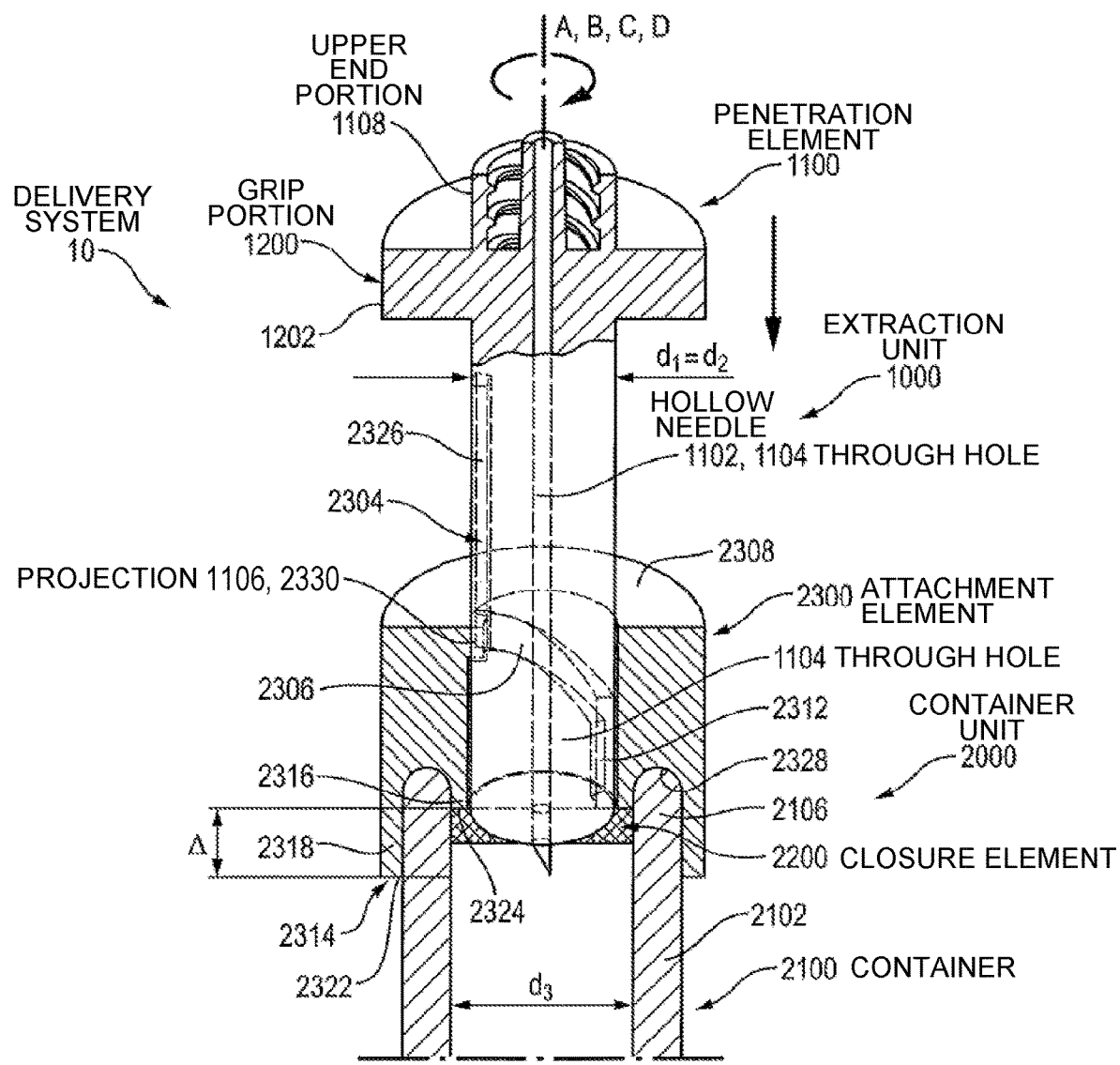
FIG. 2C is a schematic drawing of the delivery system of FIG. 2A in a completely penetrated state.
Figure 2D:
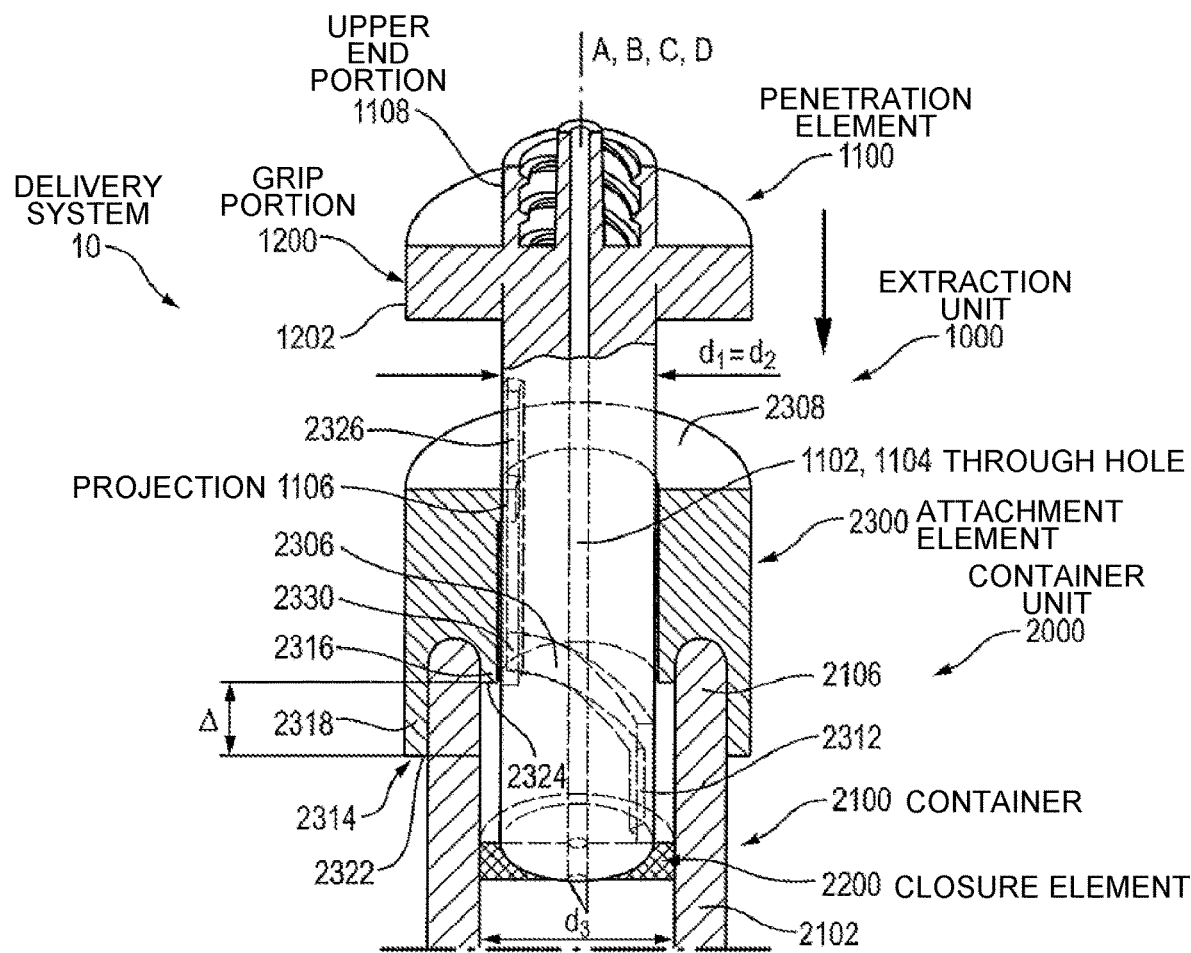
FIG. 2D is a schematic drawing of the delivery system of FIG. 2A with the closure element pushed towards the container bottom.

FIGS. 1B-1D show various stages of the penetration process, including (1) connecting the penetration element 1100, (2) screwing down the penetration element 1100, and (3) penetrating the closure element 2200 with the hollow needle 1102. FIG. 1B illustrates step (1), in which the penetration element 1100 is connected to the attachment element 2300 by inserting the projection 1106 into the upper end of the spiral groove portion 2306 of the guiding groove 2304 while holding the penetration element 1100 at the grip portion 1200. In step (2), the extraction unit 1000 is turned to lower the penetration element 1100 rotatingly along the longitudinal axes A to D (which now coincide) resulting from the link motion now established between the penetration element 1100 and the attachment element 2300. FIG. 1C illustrates step (3), in which the closure element 2200 is completely penetrated by the hollow needle 1102 after the lower surface of the penetration element 1100 comes in contact with an upper surface of the closure element 2200. The hollow needle 1102 penetrates the closure element 2200 and projects from the lower surface of the closure element 2200. In this completely penetrated state, the projection 1106 is located at point 2330, i.e., the point where the spiral groove portion 2306 connects with the straight groove portion 2312.

In the state shown in FIG. 1C, the penetration process is completed and the elliptical chamfered end face of the hollow needle 1102 is visible below the closure element 2200. By further longitudinally moving the penetration element 1100 downward, the projection 1106 is guided within the straight groove portion 2312, and the penetration element 1100 acting as a piston pushes the closure element 2200 downwards towards a container bottom 2104. The compounds stored in the container 2100 are thereby extracted in a flowing direction opposite to the movement direction and are delivered out of the delivery system 10 through the hollow needle 1102. In the first embodiment, the upper end portion 1108 is formed as a male part 1110 of a Luer lock. The upper end portion 1108 may be coupled to a female part (not shown) of an appropriate device to finally administer the compounds to a patient, for example.

FIGS. 2A-2D show states corresponding to the states shown in FIGS. 1A-1D, respectively, of a delivery system according to a second embodiment of the present invention. The second embodiment differs from the first embodiment in that the locations of the guiding groove 2304 and the projection 1106 are switched. The guiding groove 2304 is formed in the penetration element 1100, whereas the projection 1106 is formed at the surface of the through hole 2302 through the attachment element 2300. In order to emphasize that their respective tasks are identical, their reference numerals are maintained.

The guiding groove 2304 is modified slightly in the second embodiment to permit the penetration element 1100 to be connected to the attachment element 2300 and to permit the penetration element 1100 to move downward within the container 2100. The guiding groove 2304 is elongated with respect to the version of the first embodiment by a straight upper groove portion 2326 that is connected to the spiral groove portion 2306 at an upper connecting point 2328. The guiding groove 2304 is also elongated by a lower straight groove portion 2312 that is connected to the spiral groove portion 2306 at a lower connecting point 2330.

The first and second embodiments described above correspond to preferred embodiments in which the closure element 2200 is pushed by the extraction unit 1000 towards the container bottom 2104 in order to displace the medical or pharmaceutical compound from the container into the hollow needle 1102.

Figure 3A:
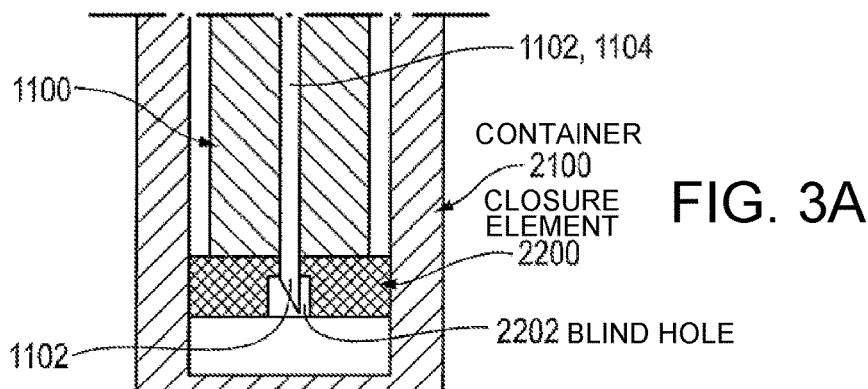
FIG. 3A is a schematic drawing showing a first variation of the shape of a closure element and a container bottom of the delivery system according to the first and second embodiments.
Figure 3B:
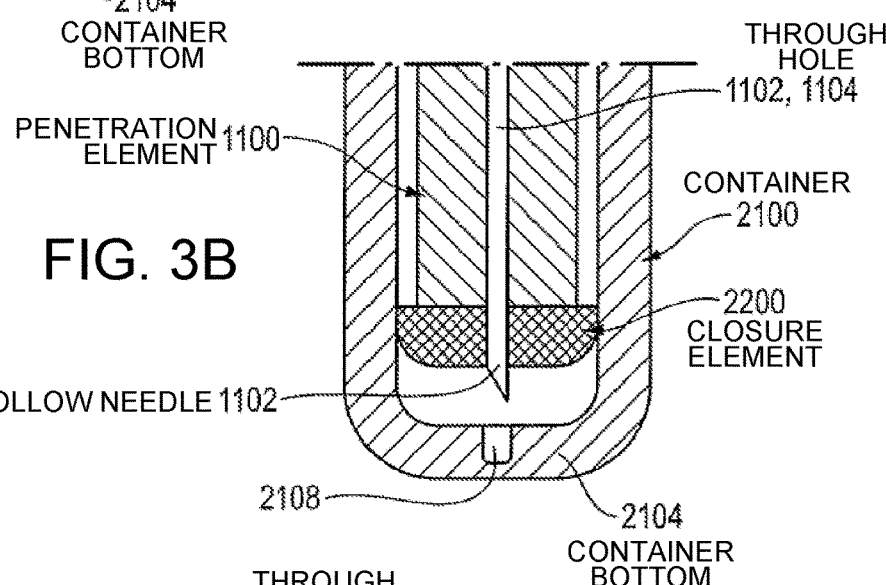
FIG. 3B is a schematic drawing showing a second variation of the shape of the closure element and the container bottom.
Figure 3C:
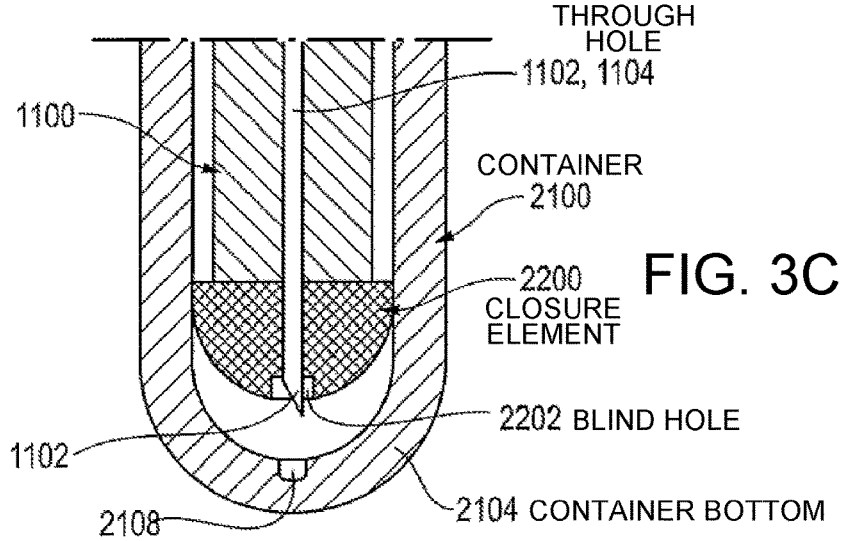
FIG. 3C is a schematic drawing showing a third variation of the shape of the closure element and the container bottom.

FIGS. 3A-3C show schematic drawings of variations of the container bottom 2104 of the container 2100. The shapes of the closure element 220 in each of the variations correspond to the shapes of the container bottom 2104.

The shapes of contact surfaces of the closure element 2200 and the container bottom 2104 correspond to each other in that any convex shape of the former is equivalent to a concave shape of the latter. The contact surfaces in FIG. 3A are both flat. The convex closure element 2200 in FIG. 3B is complementary to a flat surface with rounded edges of the container bottom 2104, which has an overall concave shape. Both corresponding surfaces in FIG. 3C are spherical. In addition, a blind hole 2202 is located in the bottom surface of the closure element 2200, or a blind hole 2108 is located in the container bottom 2104. The blind hole 2202, 2108 provides a space for the tip of the hollow needle 1102 when the penetration element 1100 is pressed all the way to the container bottom 2104 in order to reduce to a minimum the amount of compounds that cannot be extracted from the container 2100. The space provided by the blind hole 2202, 2108 also prevents damage to the tip of the hollow needle 1102 in the completely compressed state so as to allow the penetration element 1100 to be used several times. In FIG. 3A, the hollow needle 1102 projects from the closure element 2200 at most by an amount equal to the remaining thickness of the closure element 2200 in the blind hole 2202. In FIG. 3B, the hollow needle 1102 projects from the lower surface of the closure element 2200 at most by an amount equal to the depth of the blind hole 2108 formed in the container bottom 2104. The variation shown in FIG. 3C is situated between the above two extremes.

Figure 4A:
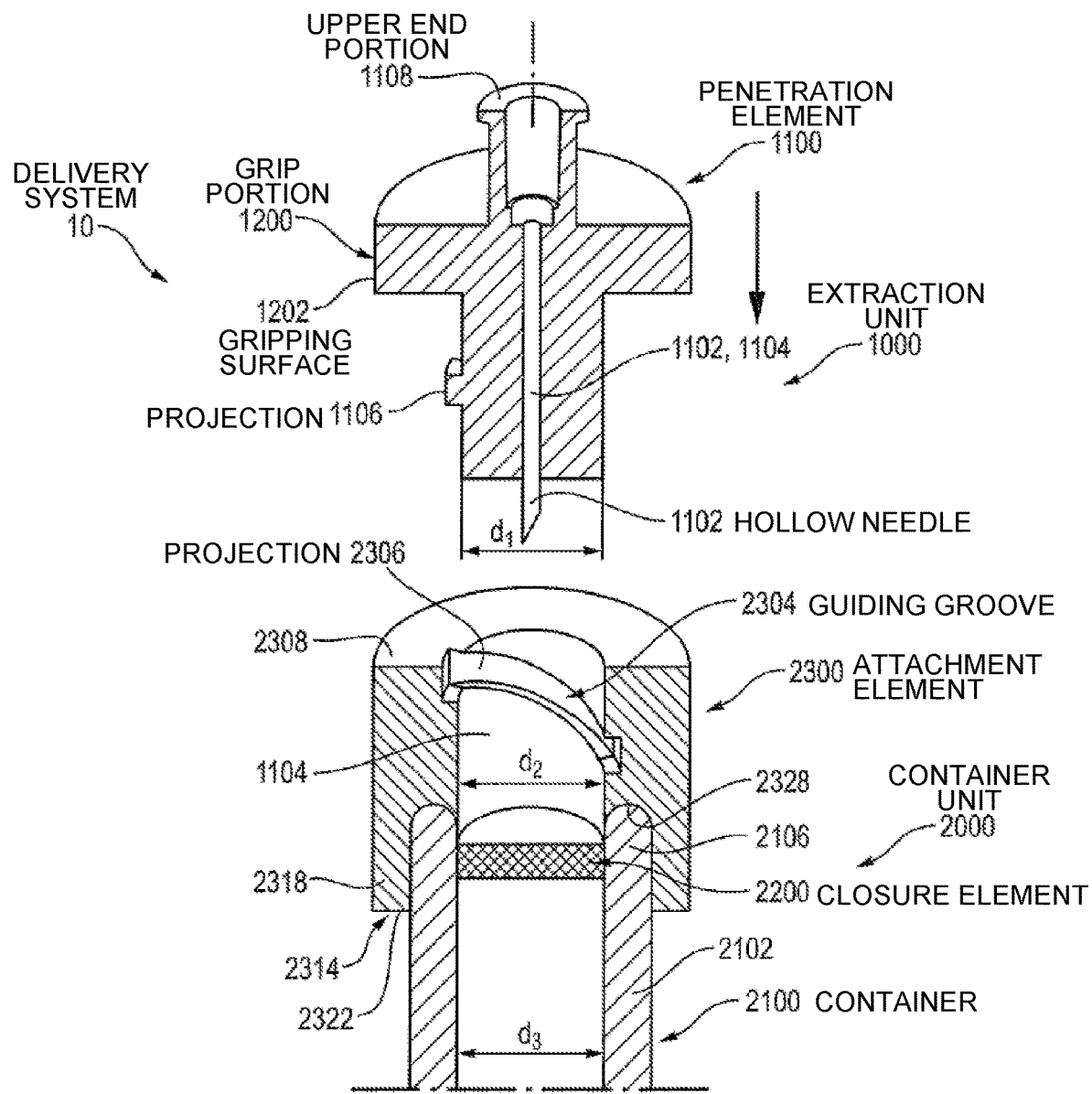
FIG. 4A is a schematic drawing of a delivery system in an initial position according to a third embodiment.
Figure 4B:
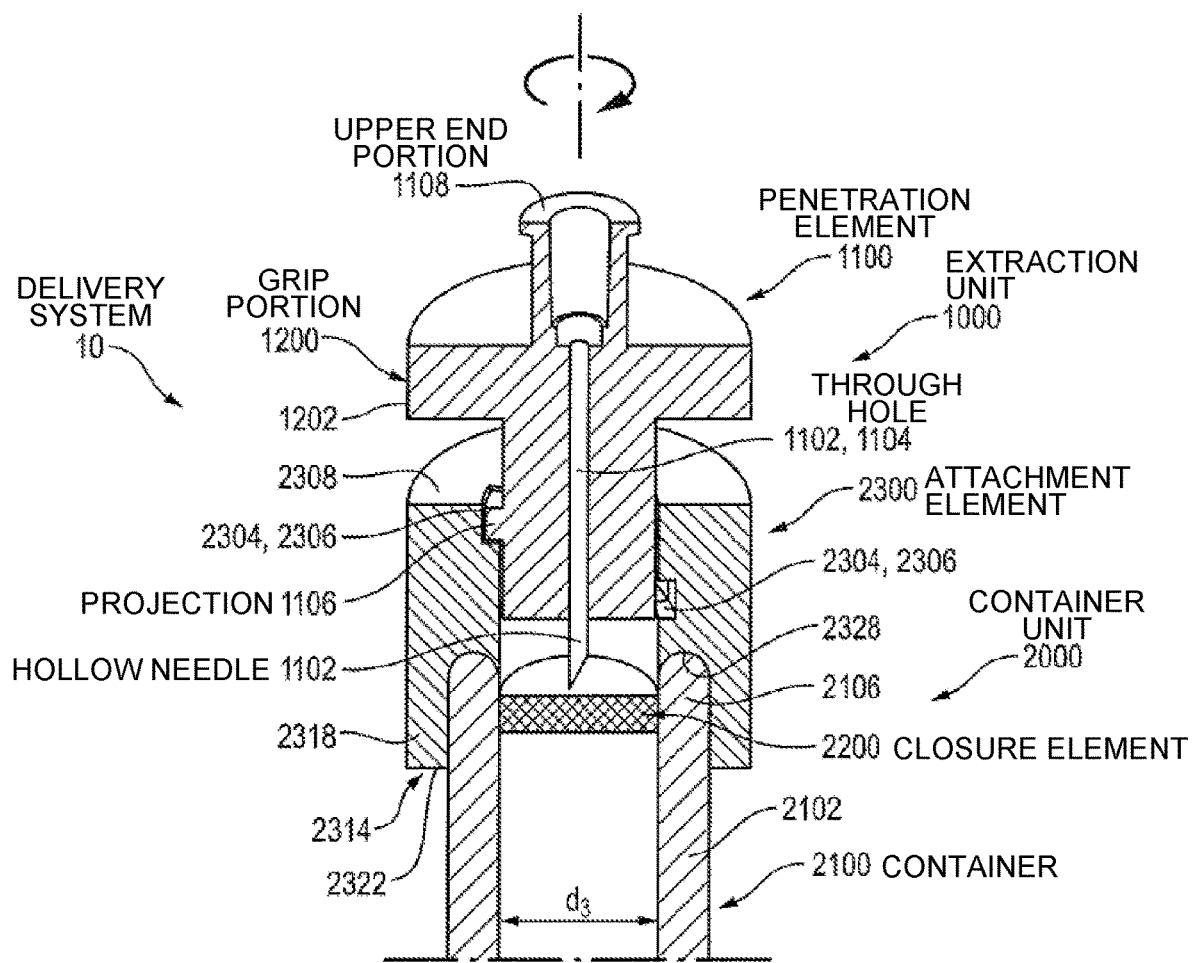
FIG. 4B is a schematic drawing of the delivery system of FIG. 4A in an intermediate state.
Figure 4C:
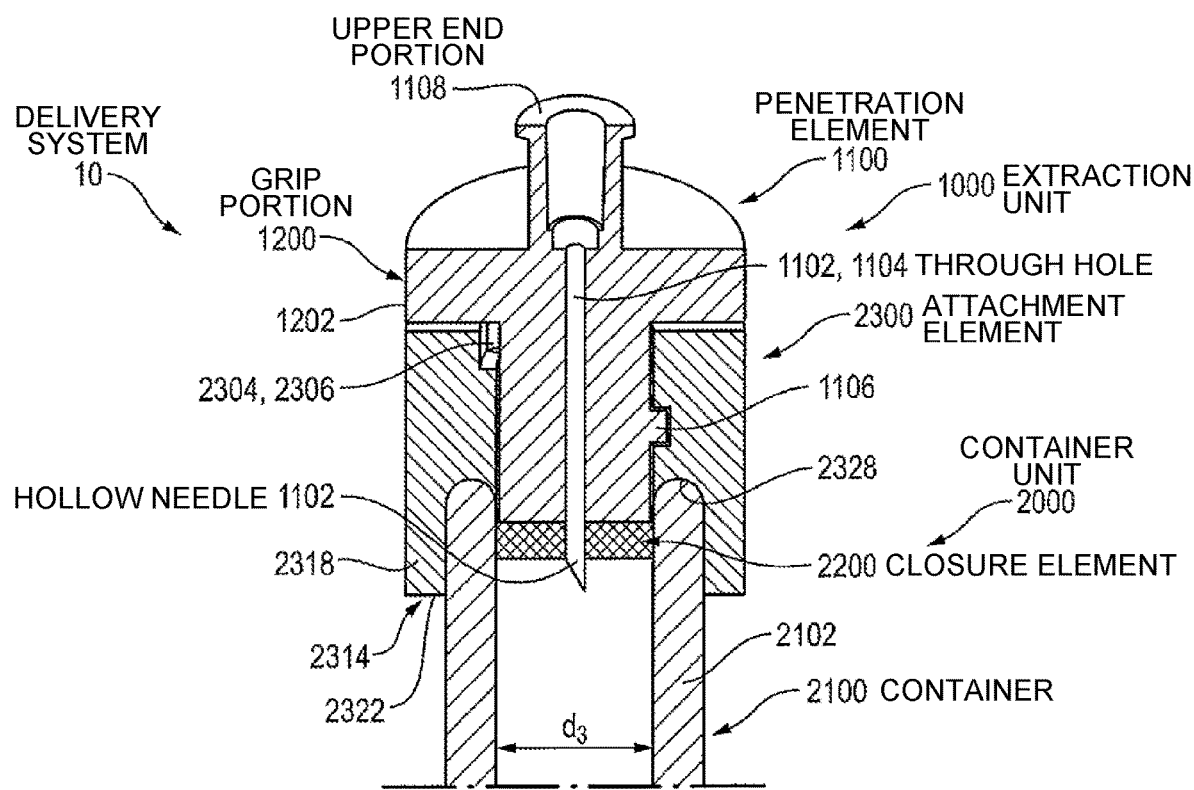
FIG. 4C is a schematic drawing of the delivery system of FIG. 4A in a completely penetrated state.
Figure 4D:
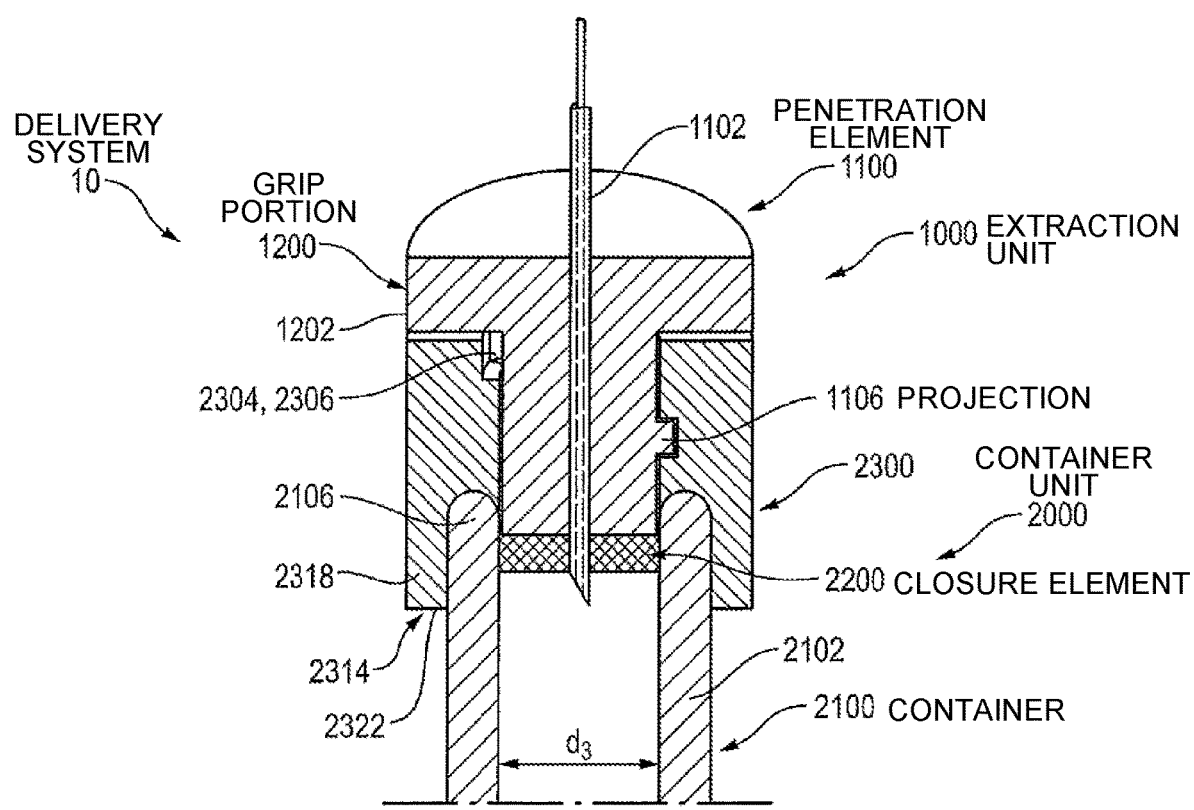
FIG. 4D is a schematic drawing of the delivery system of FIG. 4A with an alternative penetration element in a completely penetrated state.

FIGS. 4A-4C show schematic drawings of the delivery system 10 according to a third embodiment of the present invention. The essential difference between the delivery system 10 of the third embodiment and the delivery systems of the first and second embodiments is that the guiding groove 2304 includes only the spiral groove portion 2306, and includes neither the straight lower groove portion 2312 nor the straight upper groove portion 2326. As in the first embodiment, the guiding groove 2304 of the third embodiment is located in the attachment element 2300. In the third embodiment, the penetration element 1100 does not act as a piston because the closure element 2200 is not pressed downwards towards the container bottom 2104. Instead, the compounds are extracted from the container 2100 using gravity, and the delivery system 10 of the third embodiment must be oriented upside-down compared to the figures. To enable air to replace the compounds in the delivery process, either the upper end is formed as part of a Luer lock (through a male part), or the hollow needle 1102 is formed as a double cannula as shown in FIG. 4D.

Thus, the third embodiment corresponds to an alternative preferred embodiment of the present invention where the closure element 2200 remains with the extraction unit 1000 in its initial position and is not be pushed by the extraction unit 1000 towards the container bottom 2104 by overcoming the frictional force. The medical or pharmaceutical compound is drawn from the container 2100 into the hollow needle 1102 by applying negative pressure to the container via the hollow needle, or by flowing out of the container by gravitational force.

FIGS. 4A-4C illustrate that the diameters d1-d3 may all be equal. As shown in FIG. 4A, d1 is the outer diameter of the penetration element 1100, d2 is the inner diameter of the through hole 2302 of the attachment element 2300, and d3 is the inner diameter of the container 2100. Because d2 equals d3, the attachment element 2300 of the third embodiment does not have an inner portion 2316, and the lower surface 2314 is a sum of the lower end face 2322 and the surface 2328. The states shown in FIGS. 4A-4C correspond to the states of FIGS. 1A-1C and FIGS. 2A-3C.

Figure 5A:
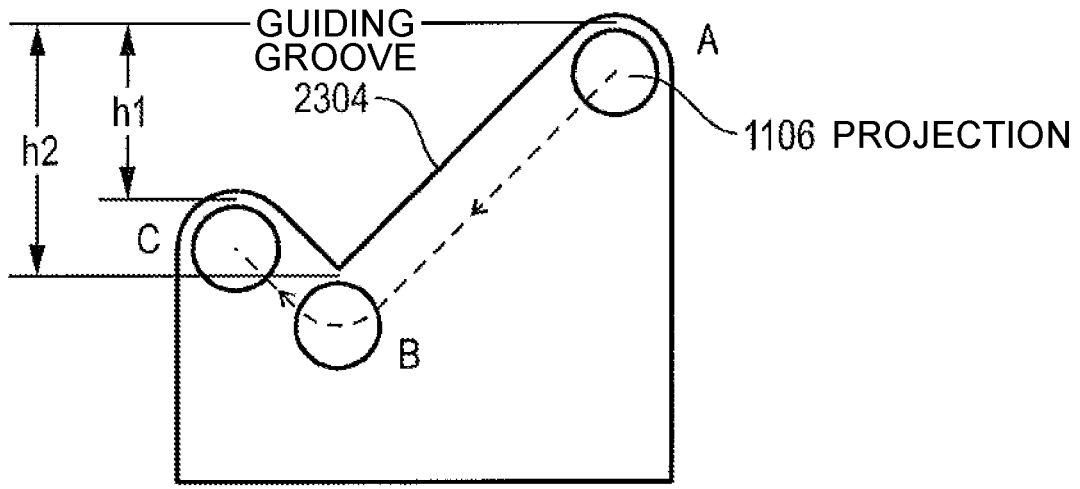
FIG. 5A is a schematic drawing illustrating a first alternative of a developed surface for a link motion of the delivery system according to the present invention.

FIG. 5A is a schematic diagram of a preferred first variation of a link motion defined as the projection 1106 follows the guiding groove 2304. The projection 1106 and the guiding groove 2304 may be part of the hollow needle supporting portion 1100 and the attachment element 2300, respectively, or vice versa. The projection 1106 may be part of the penetration element 1100 or part of the attachment element 2300. The same applies correspondingly for the guiding groove 2304. In FIG. 5A, after the projection 1106 is inserted into or coupled to the guiding groove 2304 at point A, hereafter called the starting position, the projection 1106 moves along the guiding groove 2304 by rotating the hollow needle supporting portion 1100 with respect to the attachment element 2300 first downwards by the longitudinal distance h2 to a position B and then upwards by the longitudinal distance h2−h1 to a position C. Both distances h1 and h2 are measured with respect to the starting position, as shown in FIG. 5A.

Figure 5B:
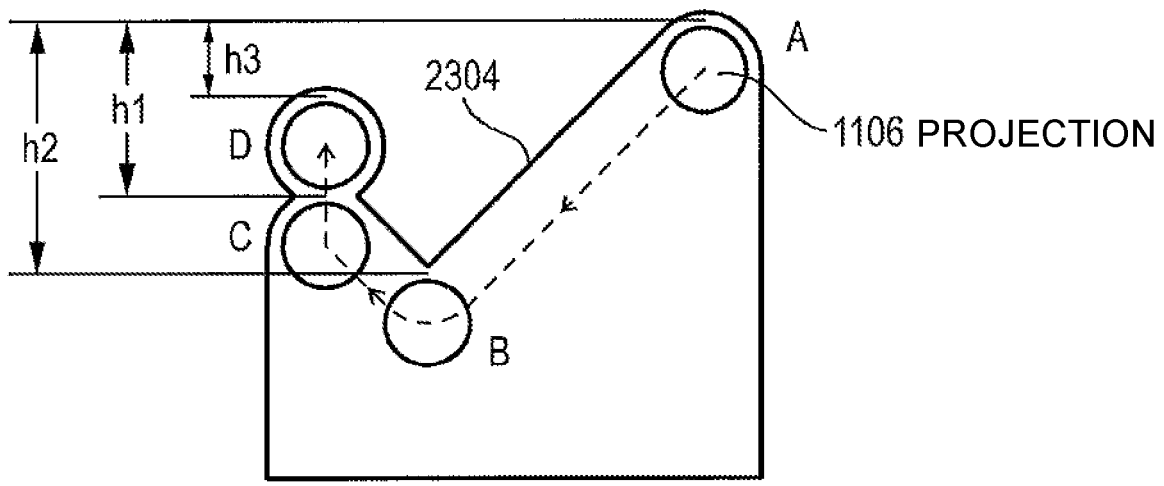
FIG. 5B is a schematic drawing illustrating a second alternative of a developed surface for the link motion of the delivery system.

FIG. 5B shows a schematic diagram of a preferred second variation of the motion link defined by the projection 1106 following the guiding groove 2304. The second variation differs from the first variation in that the position D is added. The position D is displaced with respect to position C longitudinally with respect to the longitudinal axis A and/or radially. Position D (>h3) is achieved by further rotating the penetration element 1100 with respect to the attachment element 2300. Position D is a locking position that allows a longitudinal force to be exerted on the extraction unit 1000 without returning the projection 1106 back to position B in the process of pushing the closure element 1200 downwards. As shown in FIG. 5B, h3<h1<h2.

Figure 6:
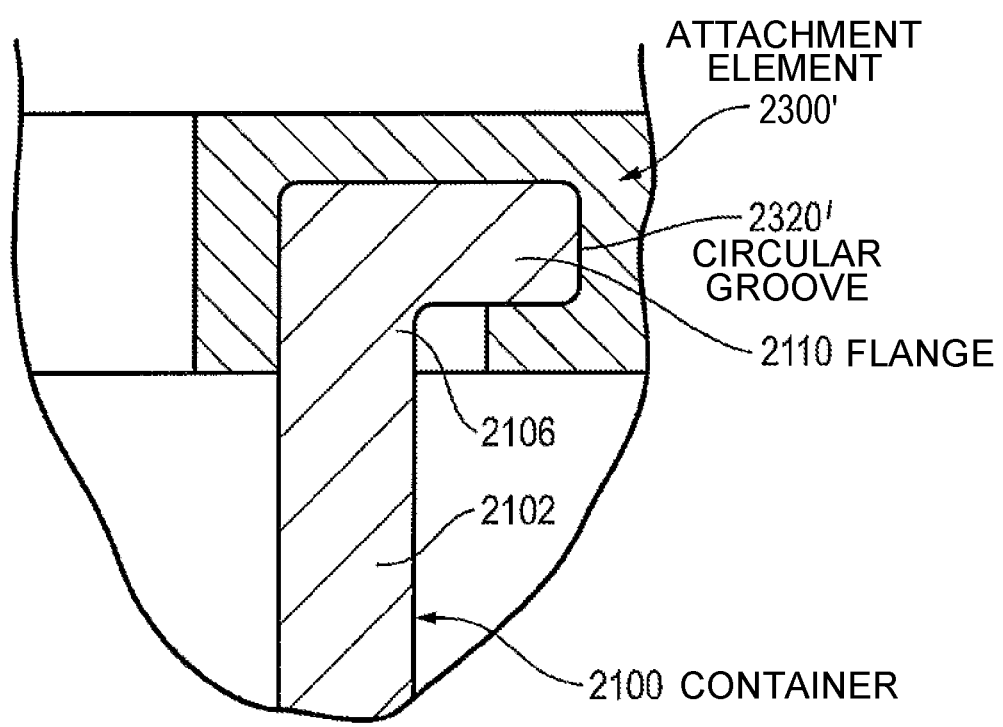
FIG. 6 is a schematic enlarged view of an alternative container having a flange portion.

FIG. 6 shows a enlarged schematic detailed view of an alternative container 2100 having a flange 2110 extending outwardly along its rim portion 2106. The flange 2110 is accommodated within a circular groove 2320' of an attachment element 2300'. In the process of attaching the attachment element 2300' to the container 2100, the attachment element 2300' is stretched and snapped over and around the flange 2110. The attachment element 2300' is shown very schematically and simplified to emphasize the circular groove 2320. The actual alternative attachment element 2300' is identical in all other structural terms with the attachment element 2300 described above.

Figure 7A:
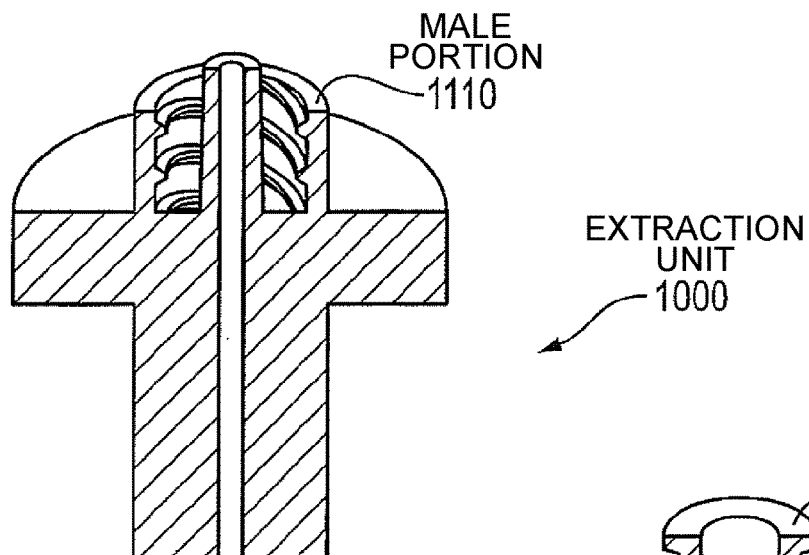
FIG. 7A to 7C are schematic drawings showing variations of a delivery system according to the present invention.
Figure 7B:
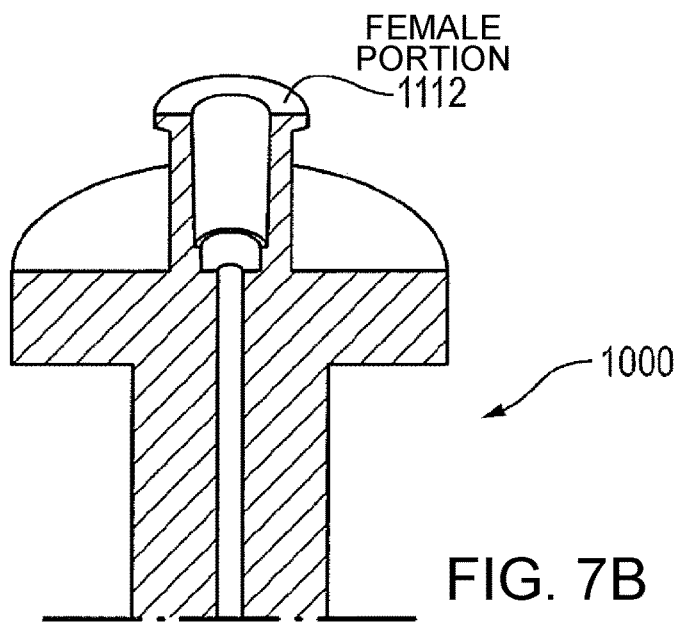
Figure 7C:
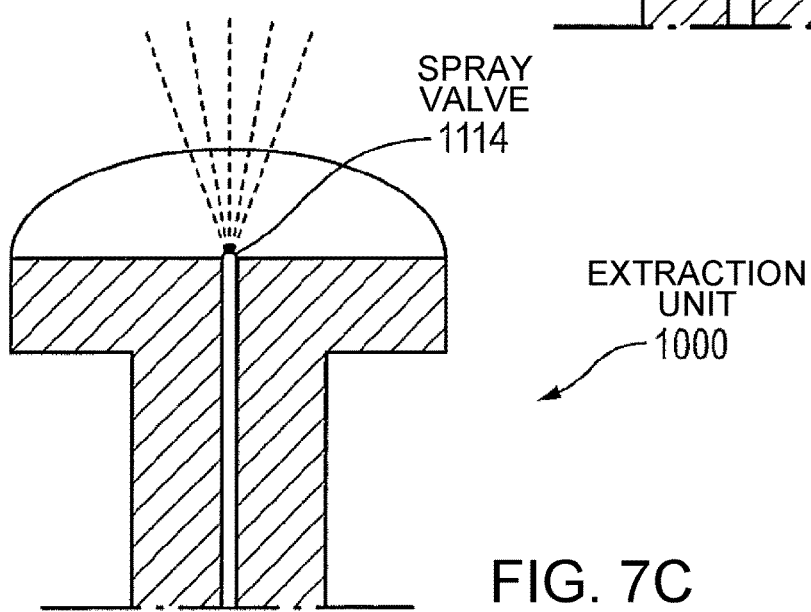

FIGS. 7A-7C show variations of the type of delivery performed by the delivery system 10. The term "type of delivery" refers to the usage or connectivity of the inventive delivery system 10. For example, the delivery system 10 may be coupled by a Luer lock connection 1110, 1112 to a second device. The Luer lock portion is formed on the extraction unit 1000 and may be a male portion 1110 as shown in FIG. 7A or a female portion 1112 as shown in FIG. 7B. The hollow needle 1102 may or may not extend up to an upper end face of the Luer lock portion 1110, 1112. As shown in FIG. 7C, the novel delivery system 10 may alternatively be used as a spraying device having a spray valve 1114 instead of a Luer lock connection. The modular design of the novel delivery system 10 allows differently shaped extraction units 1000 to be connected to the container unit 2000 depending on the desired usage.

Figure 8A:
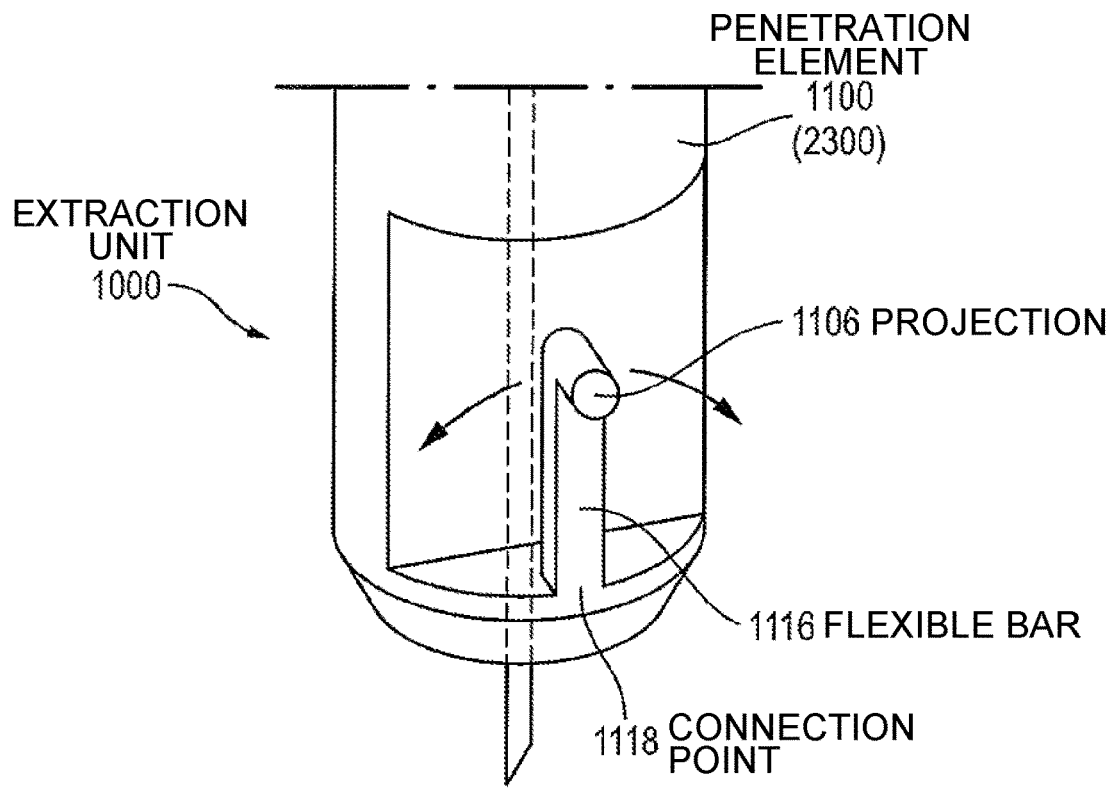
FIG. 8A is a schematic drawing illustrating a first alternative of a link motion of the delivery system according to the present invention.
Figure 8B:
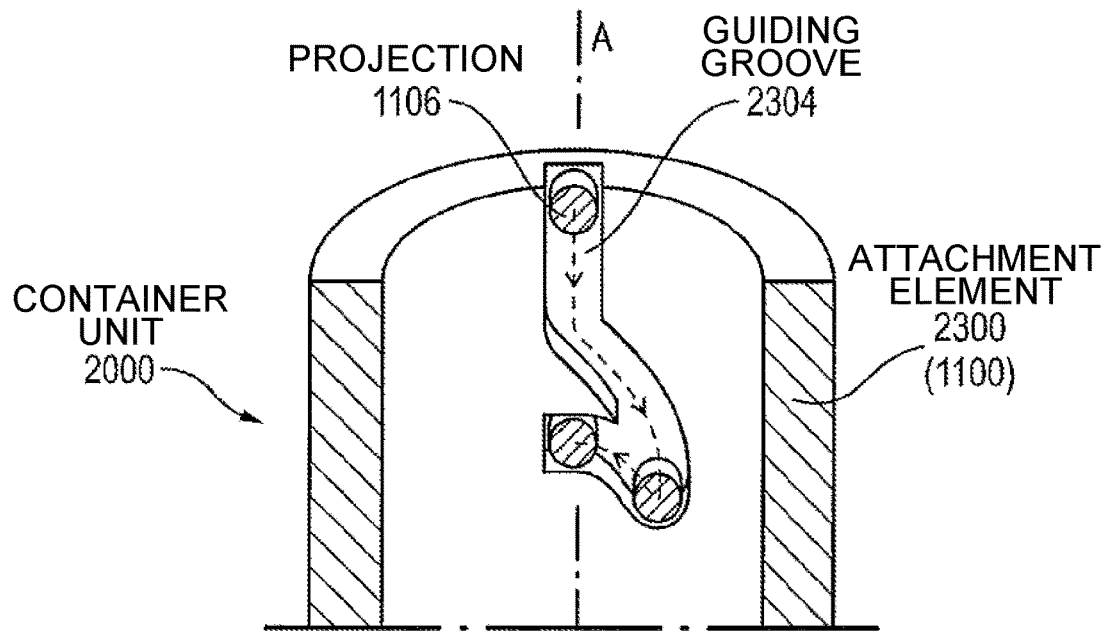
FIG. 8B is a schematic drawing illustrating a second alternative of the link motion of the delivery system.

FIGS. 8A-8B are schematic drawings illustrating an alternative link motion. In this embodiment, the link motion adopts the structure and function of a conventional ballpoint pen. The projection 1106 is flexibly connected by a flexible bar 1116 to the main body of either the first or second link motion portions, here either the penetration element 1100 or the attachment element 2300. The guiding groove 2304 is formed in the other one of the first or second link motion portions, here the attachment element 2300 or the penetration element 1100. As shown by the arrows in FIG. 8A, the flexible bar 1116 is allowed to pivot about a connection point 1118 with respect to the circumference of the main body in a plane perpendicular to the longitudinal axis. The flexible bar 1116 is integrally connected at the connection point 1118 to the main body. The guiding groove 2304 may have the shape shown in FIG. 8A, resulting in a link motion as known in principle from a ballpoint pen in which the pen refill (corresponding to the penetration element 1100) is only linearly movable (here along the longitudinal axis A). An extension of the compression piece (spring) is usually activated by the thumb of the user and moves the pen refill in and out.

Figure 8C:
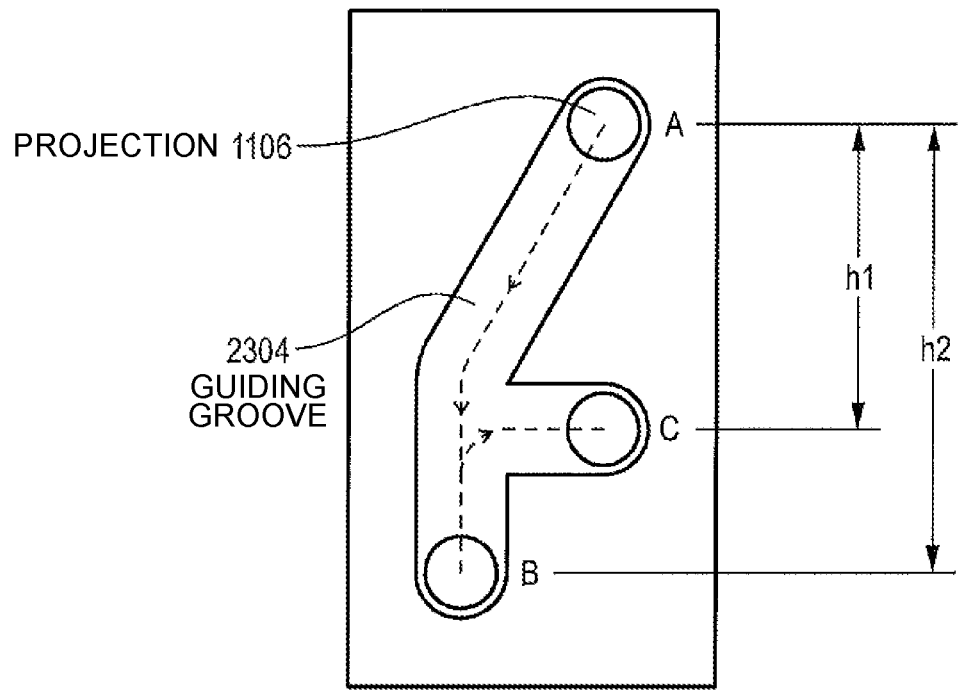
FIG. 8C is a schematic drawing illustrating a first modification of the alternatives of FIGS. 8A and 8B.
Figure 8D:
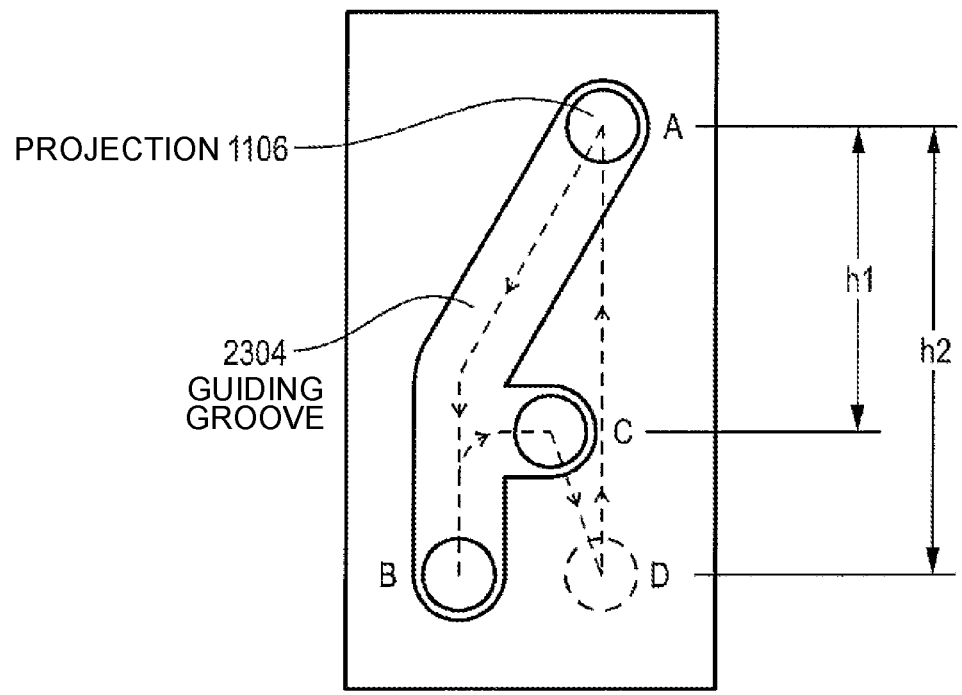
FIG. 8D is a schematic drawing illustrating a second modification of the alternatives of FIGS. 8A and 8B.

In this embodiment, as in a conventional ballpoint pen, the compression piece (extraction unit 1000) is pressed once (here moved downwards) to shift out the refill, and is shifted in by pressing the compression piece a second time. Therefore, according to this alternative, the link motion is designed in line with such a ballpoint mechanism. FIGS. 8C-8D are schematic drawings illustrating a modification of the link motion of FIGS. 8A-8B. In this modification, the link motion also follows the structure and function of a conventional ballpoint pen. The projection 1106 is flexibly connected by the flexible bar 1116 (not shown in FIGS.

8C-8D) to either the first or second link motion portions, while the guiding groove 2304 is formed in the other of the first or second link motion portions. When the extraction unit 1000 is pressed a first time, the connection point 1118 of the flexible bar 1116 is moved downwards along a line slightly shifted to the right with respect to the line defined by points A and C. During that downward movement, the flexible bar 1116 is bent because the projection 1106 is guided within the guiding groove 2304 along a trajectory shown as dashed line from A to B to C. Due to the detailed structure of the mechanism (not shown here) and provided the downward movement is not too slow, the projection 1106, which is biased by the elastic force of the flexible bar 1116, snaps into the passage to point C from a retracting movement only after having reached point B. By pressing the extraction unit 1000 a second time, the projection 1106 on the flexible bar 1116 snaps out of the guiding groove 2304 to allow the extraction unit 1000 to move back along the shifted line. As shown in FIG. 8D, the path to point C may be shortened compared to the path in FIG. 8C. In FIG. 8D, both the movement when the extraction unit 1000 is pressed a first time and the movement when the extraction unit 1000 is pressed a second time are shown by the dashed line in the direction of the arrows. All link motions described herein and shown in FIGS. 3A-3B and 8A-8D are applicable to the structures of all delivery systems described with reference to the remaining figures.

REFERENCE NUMERALS 10 delivery system
1000 extraction unit
1100 penetration element
1102 hollow needle
1104 through hole
1106 projection
1107 first link motion portion
1108 upper end portion
1110 male part of a Luer lock
1112 female part of a Luer lock
1114 spray valve
1116 flexible bar
1118 connection point
1200 grip portion
1202 gripping surface
2000 container unit
2100 container
2102 side wall
2104 container bottom
2106 upper end portion
2108 blind hole
2200 closure element
2202 blind hole
2300 attachment element
2302 through hole
2304 guiding groove
2305 second link motion portion
2306 spiral groove portion
2308 upper surface
2310 inner point
2312 straight groove portion
2314 lower surface
2316 inner portion
2318 outer portion
2320 circular groove
2322 outer end face
2324 inner end face
2326 upper groove portion
2328 upper connecting point
A longitudinal axis of penetration element 1100
B longitudinal axis of hollow needle 1102
C longitudinal axis of attachment element 2300
d1-d3 diameters Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A device, comprising:
a container adapted to contain a liquid, wherein the container has a cylindrical wall, a first end closed by a container bottom and a second end that is open, wherein the container has a central longitudinal axis;
an elastic closure disc disposed inside the container that makes fluid-tight contact with the cylindrical wall;
an attachment element attached to a rim portion of the container, wherein the rim portion forms the second end of the container, wherein the attachment element has a first overlapping portion outwardly overlapping the rim portion and a second overlapping portion inwardly overlapping the container portion fitting down longitudinally in tight contact around the rim portion, and wherein the attachment element has a guiding groove; and
a penetration element that includes a hollow needle adapted to penetrate the elastic closure disc, wherein a projection is disposed on the penetration element, and wherein the projection engages the guiding groove and guides the penetration element to move relative to the container towards the container bottom so that the hollow needle penetrates the elastic closure disc at the longitudinal axis.

2. The device of claim 1, wherein the penetration element fits into the attachment element.

3. The device of claim 1, wherein the first overlapping portion is longer than the second overlapping portion.

4. The device of claim 1, wherein the guiding groove has a spiral portion and a straight portion, and wherein the straight portion runs parallel to the central longitudinal axis.

5. The device of claim 1, wherein the penetration element includes a grip portion.

6. The device of claim 1, wherein the penetration element has a delivery end that is formed as a part of a Luer lock connector.

7. The device of claim 1, wherein a cannula extends from a delivery end of the penetration element.

8. The device of claim 1, wherein the elastic closure disc has a bottom surface with a non-planar first shape, wherein the container bottom has a non-planar second shape, and wherein the first shape and the second shape are complementary.

9. The device of claim 1, wherein the elastic closure disc has a bottom surface with a blind hole.

10. A device, comprising:
a container unit that includes a container, a elastic closure disc and an attachment element, wherein the container is adapted to contain a liquid, wherein the container has a cylindrical wall, a first end that is closed by a container bottom and a second end that is open and forms a rim portion to which the attachment element is attached, wherein the container unit has a longitudinal axis, wherein the attachment element has a first overlapping portion outwardly overlapping the rim portion and a second overlapping portion inwardly overlapping the container portion fitting longitudinally down around the rim portion in tight contact, and wherein the elastic closure disc is disposed within the container and makes a fluid-tight contact with the cylindrical wall; and an extraction unit that includes a penetration element and a hollow needle adapted to penetrate the elastic closure disc, wherein the extraction unit moves relative to the container along the longitudinal axis towards the container bottom, wherein the extraction unit includes a first link motion portion, and the container unit includes a second link motion portion, wherein one of the first link motion portion or the second link motion portion is provided with a projection and the other of the first link motion portion or the second link motion portion is provided with a guiding groove, and wherein the projection engages the guiding groove and guides the extraction unit to move relative to the container towards the container bottom so that the hollow needle penetrates the elastic closure disc at the longitudinal axis.

11. The device of claim 10, wherein the first link motion portion is disposed on the penetration element.

12. The device of claim 10, wherein the first link motion portion fits into the second link motion portion.

13. The device of claim 10, and wherein the second link motion portion is disposed on the attachment element.

14. The device of claim 13, wherein the penetration element extends through a through hole in the attachment element.

15. The device of claim 13, wherein the first overlapping portion is longer than the second overlapping portion.

16. The device of claim 10, wherein the extraction unit includes a grip portion connected to the penetration element.

17. The device of claim 10, wherein the extraction unit has a delivery end that is formed as a part of a Luer lock connector.

18. The device of claim 10, wherein a cannula extends from a delivery end of the extraction unit.

19. The device of claim 10, wherein the elastic closure disc has a bottom surface with a first shape, wherein the container bottom has a second shape, and wherein the first shape and the second shape are complementary.

20. The device of claim 10, wherein the elastic closure disc has a bottom surface with a blind hole.

* * * * *